(12) United States Patent
Bonnet et al.

(10) Patent No.: US 11,066,353 B2
(45) Date of Patent: *Jul. 20, 2021

(54) ANTIGEN DELIVERY VECTORS AND CONSTRUCTS

(71) Applicant: ALTIMMUNE UK LIMITED, London (GB)

(72) Inventors: Dominique Bonnet, Geispolsheim (FR); Carlton B. Brown, London Santa Cruz la Laguna (GT); Bertrand V. Georges, London (GB); Philip J. Sizer, Helsby (GB)

(73) Assignee: Altimmune UK Ltd, Leeds (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/286,531

(22) Filed: May 23, 2014

(65) Prior Publication Data

US 2015/0112042 A1    Apr. 23, 2015

Related U.S. Application Data

(63) Continuation of application No. 13/354,871, filed on Jan. 20, 2012, now Pat. No. 8,759,281, which is a continuation of application No. 12/700,526, filed on Feb. 4, 2010, now Pat. No. 8,110,540, which is a continuation of application No. 11/096,725, filed on Apr. 1, 2005, now Pat. No. 7,687,455.

(30) Foreign Application Priority Data

Apr. 13, 2004   (GB) .................................... 0408164

(51) Int. Cl.
| | |
|---|---|
| *C07C 55/32* | (2006.01) |
| *C07C 57/52* | (2006.01) |
| *A61K 39/21* | (2006.01) |
| *A61K 39/385* | (2006.01) |
| *C07K 14/005* | (2006.01) |
| *A61K 39/12* | (2006.01) |
| *A61K 47/54* | (2017.01) |
| *A61K 31/02* | (2006.01) |
| *A61K 38/02* | (2006.01) |
| *A61K 39/00* | (2006.01) |
| *C12N 7/00* | (2006.01) |
| *C07C 19/08* | (2006.01) |
| *C07K 2/00* | (2006.01) |

(52) U.S. Cl.
CPC ............. *C07C 57/52* (2013.01); *A61K 31/02* (2013.01); *A61K 38/02* (2013.01); *A61K 39/00* (2013.01); *A61K 39/12* (2013.01); *A61K 39/21* (2013.01); *A61K 39/385* (2013.01); *A61K 47/54* (2017.08); *C07K 14/005* (2013.01); *C12N 7/00* (2013.01); *A61K 2039/54* (2013.01); *A61K 2039/543* (2013.01); *A61K 2039/545* (2013.01); *A61K 2039/5555* (2013.01); *A61K 2039/55511* (2013.01); *A61K 2039/55566* (2013.01); *A61K 2039/60* (2013.01); *A61K 2039/6018* (2013.01); *C07C 19/08* (2013.01); *C07K 2/00* (2013.01); *C12N 2740/16022* (2013.01); *C12N 2740/16034* (2013.01); *C12N 2740/16122* (2013.01); *C12N 2740/16134* (2013.01); *C12N 2740/16322* (2013.01)

(58) Field of Classification Search
None
See application file for complete search history.

(56) References Cited

U.S. PATENT DOCUMENTS

| | | | |
|---|---|---|---|
| 3,065,141 | A | 11/1962 | Gessler et al. |
| 3,843,443 | A | 10/1974 | Fishman |
| 4,332,787 | A | 6/1982 | Homcy et al. |
| 4,689,398 | A | 8/1987 | Wu et al. |
| 4,954,444 | A * | 9/1990 | Eveleigh ................ C12N 11/08 435/180 |
| 5,021,551 | A | 6/1991 | Allen et al. |
| 5,055,562 | A | 10/1991 | Koganty |
| 5,401,634 | A | 3/1995 | Milbrath |
| 5,635,181 | A | 6/1997 | Harwood et al. |
| 5,728,578 | A | 3/1998 | Jahn et al. |
| 5,817,318 | A | 10/1998 | Sia et al. |
| 5,858,374 | A | 1/1999 | Levy |
| 5,871,746 | A | 2/1999 | Boutillon et al. |
| 5,882,645 | A * | 3/1999 | Toth ................. A61K 47/48238 424/194.1 |
| 5,919,459 | A | 7/1999 | Nacy et al. |

(Continued)

FOREIGN PATENT DOCUMENTS

| | | |
|---|---|---|
| CA | 2070254 A1 | 12/1993 |
| EP | 0 327 070 A | 8/1989 |

(Continued)

OTHER PUBLICATIONS

Sommer, Stefanie et al, "Covalent inhibition of sumo and upbiquitin specific systeine proteases by an in situ thio-alkyne addition." Bioorg. Medicinal Chem. (2013)21 p. 2511-2517.*

(Continued)

*Primary Examiner* — Fred H Reynolds
(74) *Attorney, Agent, or Firm* — Koren Anderson; Duane Morris LLP

(57) ABSTRACT

The present invention relates to fluorocarbon vectors for the delivery of antigens to immunoresponsive target cells. It further relates to fluorocarbon vector-antigen constructs and the use of such vectors associated with antigens as vaccines and immunotherapeutics in animals.

19 Claims, 10 Drawing Sheets

Specification includes a Sequence Listing.

(56) References Cited

U.S. PATENT DOCUMENTS

| | | | |
|---|---|---|---|
| 6,069,232 A | 5/2000 | Malikayl et al. | |
| 6,121,123 A | 9/2000 | Lyons et al. | |
| 6,174,532 B1 | 1/2001 | Campo et al. | |
| 6,270,778 B1 | 8/2001 | Kawakami et al. | |
| 6,413,516 B1 | 7/2002 | Chang et al. | |
| 6,491,926 B1 | 12/2002 | Morton | |
| 6,537,560 B1 | 3/2003 | Kawakami et al. | |
| 6,541,009 B1 | 4/2003 | Inglis et al. | |
| 6,548,046 B1 | 4/2003 | Lanza et al. | |
| 6,676,963 B1 | 1/2004 | Lanza et al. | |
| 6,710,035 B2 | 3/2004 | Feigner et al. | |
| 6,884,414 B1 | 4/2005 | Palese et al. | |
| 7,476,386 B1 | 1/2009 | Gras-Masse et al. | |
| 7,687,455 B2 * | 3/2010 | Bonnet | A61K 39/21 424/188.1 |
| 8,110,540 B2 * | 2/2012 | Bonnet | A61K 39/21 514/1.1 |
| 8,110,541 B2 * | 2/2012 | Bonnet | A61K 39/21 514/1.1 |
| 8,129,333 B2 * | 3/2012 | Bonnet | A61K 39/21 514/1.1 |
| 8,642,531 B2 * | 2/2014 | Bonnet | A61K 39/145 514/1.1 |
| 8,759,281 B2 * | 6/2014 | Bonnet | A61K 39/21 514/1.1 |
| 9,119,811 B2 | 9/2015 | Brown et al. | |
| 9,446,143 B2 * | 9/2016 | Bonnet | A61K 39/145 |
| 10,155,049 B2 | 12/2018 | Bonnet et al. | |
| 2005/0009008 A1 | 1/2005 | Robinson et al. | |
| 2006/0013820 A1 | 1/2006 | Bonnet et al. | |
| 2007/0059799 A1 | 3/2007 | Sette et al. | |
| 2007/0172929 A1 | 7/2007 | Maassab et al. | |
| 2007/0202100 A1 | 8/2007 | Wood et al. | |
| 2008/0145383 A1 | 6/2008 | Zauner et al. | |
| 2009/0023895 A1 | 1/2009 | Miyakawa et al. | |
| 2009/0191233 A1 | 7/2009 | Bonnet et al. | |
| 2010/0047275 A1 | 2/2010 | Stoloff et al. | |
| 2010/0183650 A1 | 7/2010 | Bonnet et al. | |
| 2010/0183708 A1 | 7/2010 | Bonnet et al. | |
| 2011/0014221 A1 | 1/2011 | Kang et al. | |
| 2012/0034259 A1 | 2/2012 | Bonnet et al. | |
| 2012/0251569 A1 | 10/2012 | Martin et al. | |
| 2012/0315293 A1 | 12/2012 | Bonnet et al. | |
| 2013/0295641 A1 * | 11/2013 | Gee | A61K 47/48338 435/188 |
| 2013/0330382 A1 | 12/2013 | Brown et al. | |
| 2014/0234356 A1 * | 8/2014 | Bonnet | A61K 39/145 424/186.1 |
| 2015/0112042 A1 | 4/2015 | Bonnet et al. | |
| 2016/0051661 A1 * | 2/2016 | Brown | A61K 39/00 424/186.1 |
| 2016/0324834 A1 | 11/2016 | Ahmed et al. | |
| 2020/0016263 A1 * | 1/2020 | Georges | A61P 31/14 |

FOREIGN PATENT DOCUMENTS

| | | |
|---|---|---|
| EP | 2190474 | 6/2010 |
| EP | 1991563 B1 | 11/2011 |
| EP | 2383284 A2 | 11/2011 |
| EP | 2383285 A2 | 11/2011 |
| FR | 2752161 A1 | 2/1998 |
| FR | 2883563 A1 | 9/2006 |
| GB | 1193378 A | 5/1970 |
| GB | 2465733 B | 12/2010 |
| RU | 2218175 C2 | 12/2003 |
| WO | WO-1994/026903 A2 | 11/1994 |
| WO | WO-1999/021541 A2 | 5/1999 |
| WO | WO-1999/045954 A1 | 9/1999 |
| WO | WO-2001/000225 A1 | 1/2001 |
| WO | WO-2001/070772 A2 | 9/2001 |
| WO | WO-2002/072627 A2 | 9/2002 |
| WO | WO-2003/040165 A2 | 5/2003 |
| WO | WO-2004/031211 A2 | 4/2004 |
| WO | WO-2005/094891 A2 | 10/2005 |
| WO | WO-2005/099752 A2 | 10/2005 |
| WO | WO-2005/120564 A2 | 12/2005 |
| WO | WO-2006/074024 | 6/2006 |
| WO | WO-2007/091030 A2 | 8/2007 |
| WO | WO-2009/027688 A1 | 3/2009 |
| WO | WO-2012/090002 A1 | 7/2012 |

OTHER PUBLICATIONS

Gripon, P. et al, "Myristylation of the hepatitis b virus large surface protein is essential for viral infectivity." Virology (1995) 213 p. 292-299.*
Boutin, Jean A., "Myristoylation." Cell Signal. (1997) 9(1) p. 15-35.*
Chai, Ning et al, "Assembly of hepatits b virus envelope proteins into a lentivirus pseudotype that infects primary human hepatocytes." J. Virology (2007) 81 p. 10897-10904.*
Mishra, A. et al, "Immune response to hepatitis b virus surface antigen peptides during hbv infection." Clin. Exp. Immunol (1992) 90 p. 194-198.*
Weber, Bernard et al, "Improved detection of hepatits b virus surface antigen by a new rapid automated assay." J. Clin. Microbiol. (1999) 37(8) p. 2639-2647.*
Leenaars, Marlies et al, "The production of polyclonal antibodies in laboratory animals." Alternatives to Laboratory Animals (1999) p. 1-28.*
Pierce biotechnology pamphlet on affinity purification, available Jan. 2004.*
Cui, Zhengrong et al, "Novel enthanol in fluorocarbon microemulsions for topical genetic immunization." Pharmaceut. Res. (2003) 20(1 )p. 16-23.*
Yamaguchi, Shigehiko et al, "O/w emulsion as formed by cholesterol-pearing pullulan." Bull. Chem. Soc. Japan. (1992) 2 p. 186-190.*
Translation of Yamaguchi et al, Bull. Chem. Soc. Japan. (1992) 2 p. 186-190.*
Chang, Byeong S. et al, "Physical factors affecting the storage stability of freeze dried interleukin 1 receptor antagonist: glass transition temperature." Arch. Biochem. Biophys. (1996) 331(2) p. 249-258.*
MacKay, J. Andrew and Szoka, Francis C., "Hiv tat protein transduction domain mediated cell binding and intracellular delivery of nanoparticles." J. Dispers. Sci. Technol. (2003) 24(3) p. 465-473.*
Pardridge, William M., "Drug and gene targeting to the brain with molecular trojan horses." Nat. Rev. (2002) 1 p. 131-139.*
Yamaguchi, Shigehiko et al, "O/w-emulsion as formed by cholesterol-bearing pullulan." Bull. Chem. Soc. Japan (1992) 2 p. 186-190. This reference is in Japanese; please note that an English language translation is attached.*
Baczko, Krystyna et al, "Synthesis and surfactant properties of symmetric and unsymmetric sulfosuccinic diesters, aerosol-ot homologues." J. Chem. Soc. Perkin Trans. 2 (2001) 2179-2188.*
Harris, D. P. etal, "Immunogenicity of peptides forb cells is not impaired by overlapping t-cell epitope topology." Immunol. (1996) 88 p. 348-354.*
Knoll, Gerd et al, "Fusion of liposomes with the plasma membrane of epithelial cells: fate of inocrporated lipids as follwed by freeze fracture and autoradiography of plastic sections." J. Cell Biol. (1988) 107 (6 pt2) p. 2511-2521.*
The IEDB analysis resource, T-cell epitope prediction tools (http://tools.iedb.org/main/tcell/, accessed Feb. 27, 2020.*
Reddehause, Matthias J. et al; "A pentapeptide as minimal antigenic determinant for mhc class I restricted t lymphocytes." Nat. (1989) 337 p. 651-653.*
Sanches-Triincado, Jose L. et al; "Fundamentals and methods fort-and b-cell epitope prediction." J. Immunol. Res. (2017) article ID 2380160.*
Alatrakchi et al. (2002) "Strong CD4 Th1 responses to HIV and hepatitis C virus in HIV-infected long-term non-progressors co-infected with hepatitis C virus," AIDS 16(5):713-717.
Alexander et al. (1997) "Derivation of HLA-A11/K$^b$ Transgenic Mice: Functional CTL Repertoire and Recognition of Human A11-Restricted CTL Epitopes," J. Immunol. 159(10):4753-4761.

(56) References Cited

OTHER PUBLICATIONS

Alix (1999) "Predictive estimation of protein linear epitopes by using the program PEOPLE," Vaccine 18(3-4):311-314.
Bastin et al. (1987) "Use of Synthetic Peptides of Influenza Nucleoprotein to Define Epitopes Recognized by Class I-Restricted Cytotoxic T Lymphocytes," J. Exp. Med. 165:1508-1523.
Beebe et al. (2008) "Formulation and characterization of a ten-peptide single vial vaccine, EP-2101, designed to induce cytotoxic T-lymphocyte responses for cancer immunotherapy" Human Vaccines, 4(3):210-218.
BenMohamed et al. (2003) "Identification of novel immunodominant CD4+ THL-type T-cell peptide epitopes from herpes simplex virus glycoprotein D that confer protective immunity," J. of Virology 77(17):9463-9473.
Berkhoff et al. (2005) "Functional Constraints of Influenza A Virus Epitopes Limit Escape from Cytotoxic T Lymphocytes," J. Virol.. 79(17): 11239-11246.
Boaz et al. (2002) "Presence of HIV-1 Gag-specific IFN-gamma+ IL-2+ and CD28+IL-2+ CD4 T cell responses is associated with nonprogression in HIV-1 infection," J. of Immunology 169:6376-6385.
Bodmer et al. (1989) "Class I cross-restricted T cells reveal low responder allele due to processing of viral antigen," Nature 337:653-655.
Bonnet et al. (2005) "Effect of Glycoamphiphiles on the Solubilization and Dendritic Cell Uptake of a Lipopeptide: A Preliminary Study" Mol. Pharm., 2(5):420-427.
Boon et al. (2005) "Functional profile of human influenza virus-specific cytotoxic T lymphocyte activity is influenced by interleukin-2 concentration and epitope specificity," Clin. Exp. Immunol. 142:45-52.
Cheuk et al. (2005) "Strong memory $CD8^+T$ cell responses against immunodominant and three new subdominant HLA-B27-restricted influenza a CTL epitopes following secondary infection of HLA-B27 transgenic mice," Cellular Immunology 234:110-123.
Crowe et al. (2006) "Identification of protective and non-protective T cell epitopes in influenza," Vaccine 24:452-456.
Database Uniprot Nov. 1, 1996 (Nov. 1, 1996), Castrucci M et al.: "Genetic reassortment between avian and human influenza A virus" XP002442455 accession No. Q67194.
Database WPI Week 200416; Thomson Scientific, London, GB; AN 2004-165290; XP002508268 (2 Pages).
De Groot et al. (1997) "An Interactive Web Site Providing Major Histocompatibility Ligand Predictions: Applications to HIV Research," AIDS Res. and Human Retroviruses 13(7):529-531.
Deckert, C.A. (1980) "Pattern Etching of CVD S13N4/5102 Composites in HF/Glycerol Mixtures," Journal of the Electrochemical Society 127(2):2433-2438.
Deliyannis et al. (2002) "Induction of Long-Term Memory CD8+ T Cells for Recall of Viral Clearing Responses against Influenza Virus," J. of Virology 76(9):4212-4221.
Deres et al. (1989) "In vivo priming of virus-specific cytotoxic T lymphocytes with synthetic lipopeptide vaccine" Nature, 342:561-564.
Do et al. (2008) "Broad T cell immunity to the LcrV virulence protein is induced by targeted delivery to DEC-205/CD205-positive mouse dendritic cells" Eur. J. Immunol., 38:20-29.
Doolan et al. (2000) "HLA-DR-Promiscuous T Cell Epitopes from *Plasmodium falciparum* Pre-Erythrocytic-Stage Antigens Restricted by Multiple HLA Class II Alleles," J. Immunol. 165:1123-1137.
English Translation and Original Search Report dated Feb. 8, 2012 for Taiwanese Patent Application No. 097133417 (Taiwanese counterpart of PCT/GB2005/001279, Immune Targeting Systems, 2 pages).
EP Search Report for Application No. EP 05 72 9595 dated Jan. 26, 2009 (5 pages).
Europharmatoday website (http://www.europharmatoday.com/2009/08/startup-profile-immune-targeting-systems-ltd-synthetic-vaccines-against-mutating-viruses.html, accessed May 11, 2011).

Faroux-Corlay et al. (2000) "Synthesis of single- and double-chain fluorocarbon and hydrocarbon galactosyl amphiphiles and their anti-HIV-1 activity," Carbohydrate Res. 327:223-260.
Fayolle et al. (2004) "*Bordetella pertussis* adenylate cyclase delivers chemically coupled CD8+ T-cell epitopes to dendritic cells and elicits CTL in vivo" Vaccine, 23:604-614.
Felix et al. (1995) "Pegylated peptides. IV. Enhanced biological activity of site-directed pegylated GRF analogs" Int. J. Pept. Protein Res., 46:253-264.
Filippov et al. (2002) "Use of benzloxycarbonyl (Z)-based fluorophillic taging reagents in the purification of synthetic peptide," Tet. Let., 43, 7809-7812.
Frahm et al. (2007) "Extensive HLA class I allele promiscuity among viral CTL epitopes," Eur. J. Immunol. 37:2419-2433.
Gahery-Segard et al. (2000) "Multiepitopic B- and T-Cell Responses Induced in Humans by a Human Immunodeficiency Virus Type 1 Lipopeptide Vaccine," J. of Virology 74(4):1694-1703.
Gahery-Segard et al. (2003) "Long-Term Specific Immune Responses Induced in Humans by a Human Immunodeficiency Virus Type 1 Lipopeptide Vaccine: Characterization of CD8+-T-Cell Epitopes Recognized," J. of Virology 77(20):11220-11231.
Genbank accession No. AAB62620. Oct. 2005.
Genbank accession No. AAL32169. Nov. 2001.
Genbank accession No. NP_626519. Apr. 2006.
Gianfrani et al. (2000) "Human Memory CTL Response Specific for Influenza A Virus is Broad and Multispecific," Hum. Immunol. 61:438-452.
Gileadi et al. (1999) "Effect of epitope flanking residues on the presentation of N-terminal cytotoxic T lymphocyte epitopes," Eur J Immunol. 29(7):2213-22.
Gileadi et al. (1999) "Generation of an Immunodominant CTL Epitope Is Affected by Proteasome Subunit Composition and Stability of the Antigenic Protein," J. Immunol. 163:6045-6052.
Gotch et al. (1987) "Cytotoxic T lymphocytes recognize a fragment of influenza virus matrix protein in association with HLA-A2," Nature 326:881-882.
Hackett et al. (2005) "Vaccine Adjuvants," Chapter 10 pp. 193-219.
Hall et al. (1981) "Variation in Nucleotide Sequences Coding for the N-terminal Regions of the Matrix and Nonstructural Proteins of Influenza a Viruses," J. Virol. 38(1):1-7.
HIV Databases at Los Alamos National Laboratory (http://www.hiv.lanl.gov/content index) printed Oct. 3, 2007.
HIV Immunology Database: Compendia at Los Alamos National Laboratory (http://www.hiv.lanl.gov/content/immunology/compendium.html) printed Oct. 3, 2007.
HIV Molecular Immunology Database at Los Alamos National Laboratory (http://www.hiv.lanl.gov/content/immunology/index.html) printed Oct. 3, 2007.
Idemyor (2003) "Human immunodeficiency virus: scientific challenges impeding candidate vaccines," HIV Clin. Trial, 4:421-424.
International Search Report for PCT/GB11/001781 (Immune Targeting Systems), dated Apr. 10, 2012 (4 pages).
International Search Report for PCT/GB2005/001279, dated Sep. 12, 2005 (7 pages).
International Search Report for PCT/GB2008/002930 dated Dec. 16, 2008 (3 pages).
Internet Search Engine search for "Los Alamos National Laboratory Database" at Los Alamos National Laboratory (http://www.google.com) printed Oct. 3, 2007.
Jameson et al. (1998) "Human cytotoxic T-lymphocyte repertoire to influenza A viruses," Journal of Virology 72(11):8682-8689.
Jin et al. (2005) "Two residues in the hemagglutinin of A/Fujian/411/02-like influenza viruses are responsible for antigenic drift from A/Panama/2007/99," Virology 336:113-119.
Jones et al. (2005) "Characterisation of cell-penetrating peptide-mediated peptide delivery" Br. J. Pharmacol., 145:1093-1102.
Koch et al. (2005) "The crystal structure of human CD1d with and without alpha-galactosylceramide," Nature Immunology 6(8):819-826.
Korber et al. (2003) "HIV Immunology and HIV/SIV Vaccine Databases" 1:343, 508, 661, 1042-1044.
Krafft et al. (2009) "Chemistry, Physical Chemistry, and Uses of Molecular Fluorocarbon-Hydrocarbon Diblocks, Triblocks, and Related

(56) References Cited

OTHER PUBLICATIONS

Compounds—Unique "Apolar" Components for Self-Assembled Colloid and Interface Engineering" Chem. Rev., 109:1714-1792.
Lawson et al. (1992) "Nucleotide Sequence Changes in the Polymerase Basic Protein 2 Gene of Temperature-Sensitive Mutants of Influenza A Virus," Virology 191:506-510.
Linnemann et al. (2000) "Detection and Quantification of CD4+T Cells with Specificity for a New Major Histocompatibility Complex Class II-Restricted Influenza A Virus Matrix Protein Epitope in Peripheral Blood of Influenza Patients," J. Virol. 74(18):8740-8743.
Lu et al. (2004) "Therapeutic dendritic-cell vaccine for chronic HIV-1 infection," Nature Medicine 10(12):1359-1365.
Macken et al. (2001) "The value of a database in surveillance and vaccine selection" Congress Series 1219:103-106.
Maksyutov et al. (1993) "ADEPT: a computer program for prediction of protein antigenic determinants," Comput. Appl. Biosci. 9(3):291-297.
Marsh et al. (2000) "The HLA Facts Book," Chapter 11 pp. 61-72.
Mortara et al. (1999) "Type 1 CD4+ T-Cell Help is Required for Induction of Antipeptide Multispecific Cytotoxic T Lymphocytes by a Lipopeptidic Vaccine in Rhesus Macaques," J. of Virology 73(5):4447-4451.
Nijman et al. (1993) "Identification of peptide sequences that potentially trigger HLA-A2.1—restricted cytotoxic T lymphocytes," Eur. J. Immunol. 23:1215-1219.
Notice of Opposition and Statement of Facts and Arguments in Support of Opposition filed on Aug. 23, 2012 in EP Patent No. 1991563 owned by PepTcell Limited (corresponds to PepTcell's PCT/GB2007/000383) (31 pages).
Odorico et al. (2003) "BEPITOPE: predicting the location of continuous epitopes and patterns in proteins," J. Mol. Recognit. 16(1):20-22.
Opposition statement against related Chilean Application No. 2559-2008 by Asociacion Nacional de Laboratorios Farmaceuticos AG (in Spanish) and its English translation (7 pages).
Ozer et al. (1999) "Synthesis of perfluoroalkyltated beta-alanine and some peptide derivatives: an access to original surfactants" Amino Acids, 16:381-389.
Panina-Bordignon et al. (1989) "Universally immunogenic T cell epitopes: promiscuous binding to human MHC class II and promiscuous recognition by T cells," Eur. J. Immunol. 19:2237-2242.
Parker et al. (1992) "Sequence Motifs Important for Peptide Binding to the Human MHC Class I Molecule, HLA-A2," J. Immunol. 149(11):3580-3587.
Pellequer et al. (1993) "PREDITOP: A program for antigenicity prediction," J. Mol. Graph. 11(3):204-10.
Perrie et al.(2007) "Recent developments in particulate-based vaccines" Recent Pat. Drug Deliv. Formul., 1(2):117-129.
Plotnicky et al. (2003) "The immunodominant influenza matrix T cell epitope recognized in human induces influenza protection in HLA-A2/Kb transgenic mice," Virology 309:320-329.
Rammensee (1995) "Chemistry of Peptides Associated with MHC Class I and Class II Molecules," Current Opinion in Immunology 7:85-96.
Rammensee et al. (1999) "SYFPEITHI: database for MHC ligands and peptide motifs," Immunogenetics 50:213-219.
Reichel, et al. (1999) "Stereochemical Dependence of the Self-Assembly of the Imunoadjuvants $Pam_3Cys$ and $Pam_3Cys$-Ser" J. Am. Chem. Soc. 121:7989-7997.
Reyes et al. (1991) "Binding of Radioiodinated Influenza Virus Peptides to Class I MHC Molecules and to Other Cellular Proteins As Analyzed by Gel Filtration and Photoaffinity Labeling," Mol. Immunol. 28(4-5):341-348.
Riess et al. (1991) "Highly Effective Surfactants with Low Hemolytic Activity," Adv. Mater. 3(5):249-251.
Rosenberg et al. (1997) "Vigorous HIV-1-specific CD4+ T cell responses associated with control of viremia," Science 278:1447-1450.
Samad et al. (2007) "Liposomal drug delivery systems: an update review" Current Drug Deliv., 4:297-305.
Scheibenbogen et al. (1997) "A Sensitive Elispot Assay for Detection of CD8+ T Lymphocytes Specific for HLA Class I-binding Peptide Epitopes Derived from Influenza Proteins in the Blood of Healthy Donors and Melanoma Patients," Clin. Cancer Res. 3:221-226.
Schlaphoff et al. (2007) "Functional and Phenotypic Characterization of Peptide-Vaccine-Induced HCV-specific CD8+ T Cells in Healthy Individuals and Chronic Hepatitis C Patients," Vaccine 25 (37-38): 6793-6806.
Schmittel et al. (2001) "Application of the IFN-γ Elispot assay to quantify T cell responses against proteins," J. Immunol. Methods 247:17-24.
Sette et al. (1998) "HLA supertypes and supermotifs: a functional perspective on HLA polymorphism," Current Opinion in Immunology 10:478-482.
Speiser et al. (2005) "Rapid and strong human CD8+ T cell responses to vaccination with peptide, IFA, and CpG oligodeoxynucleotide 7909," J. of Clin. Investigation 115(3):739-746.
Sugimoto et al. (1993) "Peptide Vaccine," Cell Technology 12(1): 58-63, 74. Original article in Japanese with English translation attached (20 pages).
Takeshita (1995) "Molecular Analysis of the Same HIV Peptide Functionally Binding to Both a Class I and a Class II MHC Molecule," J. Immunol. 154:1973-1986.
Tang et al. (2005) "Isolation and Characterization of H3N2 Influenza A Virus from Turkeys," Avian Diseases 49:207-213.
Taubenberger et al. (1997) "Initial Genetic Characterization of the 1918 "Spanish" Influenza Virus," Science 275:1793-1796.
Thimme et al. (2001) "Determinants of viral clearance and persistence during acute hepatitis C virus infection," J. Exp. Med. 11:1395-1406.
Third Party Observations submitted in EP07712678.7 owned by PepTcell Limited (EP Patent No. 1991563, corresponds to PepTcell's PCT/GB2007/000383) filed with European Patent Office dated Dec. 17, 2008 (13 pages).
Thomas et al. (2006) "Cell-Mediated Protection in Influenza Infection," Emerg. Infect. Dis. 12(1):48-54.
Thust et al. (2003) "Protease-catalyzed peptide synthesis for the site-specific incorporation of alpha-fluoroalkyl amino acids into peptides," J. Organic Chem. 68(6):2290-2296.
Voeten et al. (2001) "Antigen processing for MHC class I restricted presentation of exogenous influenza A virus nucleoprotein by B-lymphoblastoid cells," Clin. Exp. Immunol. 125:423-431.
Wang et al. (2007) "CTL epitopes for influenza A including the H5N1 bird flu; genome-, pathogen-, and HLA-wide screening," Vaccine 25(15):2823-2831.
Written Opinion of the International Searching Authority for PCT/GB2007/000383 (PepTcell Limited), dated Aug. 7, 2008 (10 pages).
Written Opinion of the International Searching Authority, International Application No. PCT/GB2008/002930 (Immune Targeting Systems), dated Feb. 28, 2010 (5 pages).
Yang et al. (2005) "Expression of HLA-DP0401 Molecules for Identification of DP0401 Restricted Antigen Specific T Cells," J. Clin. Immunol. 25(5):428-436.
Yang et al. (2006) "Multiplex mapping of CD4 T cell epitopes using class II tetramers," Clinical Immunology 120:21-32.
Zhong et al. (2003) "Genome-wide Characterization of a Viral Cytotoxic T Lymphocyte Epitope Repertoire," J. Biol. Chem. 278(46):45135-45144.
"Solvent Systems and Their Selection in Pharmaceutics and Biopharmaceutics," Springer (2007) Augustijns, P. And Brewster, M., eds. "Chapter I. Principles of Solubility," Gong et al., pp. 1-27.
U.S. Appl. No. 11/096,725, Antigen Delivery Vectors and Constructs, filed Apr. 1, 2005, Granted, U.S. Pat. No. 7,687,455.
U.S. Appl. No. 12/207,828, Antigen Delivery Vectors and Constructs, filed Sep. 10, 2008, Granted, U.S. Pat. No. 8,129,333.
U.S. Appl. No. 12/700,526, Antigen Delivery Vectors and Constructs, filed Feb. 4, 2010, Granted, U.S. Pat. No. 8,110,540.
U.S. Appl. No. 12/700,566, Antigen Delivery Vectors and Constructs, filed Feb. 4, 2010, Granted, U.S. Pat. No. 8,110,541.
U.S. Appl. No. 13/354,871, Antigen Delivery Vectors and Constructs, filed Jan. 20, 2012, Granted, U.S. Pat. No. 8,759,281.

(56) References Cited

OTHER PUBLICATIONS

U.S. Appl. No. 12/201,894, Influenza Antigen Delivery Vectors and Constructs, filed Aug. 29, 2008, Granted, U.S. Pat. No. 8,642,531.
U.S. Appl. No. 14/139,293, Influenza Antigen Delivery Vectors and Constructs, filed Dec. 23, 2013, Granted, U.S. Pat. No. 9,446,143.
U.S. Appl. No. 15/242,682, Influenza Antigen Delivery Vectors and Constructs, filed Aug. 22, 2016, Granted, U.S. Pat. No. 10,155,049.
U.S. Appl. No. 16/186,558, Influenza Antigen Delivery Vectors and Constructs, filed Nov. 11, 2018, Pending, US 2019- 0142951.
U.S. Appl. No. 13/977,265, Fluorocarbon-Linked Peptide Formulation, filed Aug. 15, 2013, Granted, U.S. Pat. No. 9,119,811.
U.S. Appl. No. 14/807,606, Fluorocarbon-Linked Peptide Formulation, filed Jul. 23, 2015, Granted, U.S. Pat. No. 10,729,759.
U.S. Appl. No. 16/909,040, Fluorocarbon-Linked Peptide Formulation, filed Jun. 23, 2020, Pending, Not yet published.
U.S. Appl. No. 14/655,041, Vaccines Against Hepatitis B Virus, filed Jun. 23, 2015, Granted, U.S. Pat. No. 10,300,132.
U.S. Appl. No. 16/423,149, Vaccines Against Hepatitis B Virus, filed May 27, 2019, Pending, US 2020-0016263.

\* cited by examiner

| Peptide | CMC (mg/l) | CMC (nmol/ml) |
|---|---|---|
| ENV | None | None |
| FAVS-1-ENV | 15 | 1.6 |
| FAVS-3-ENV | 15 | 1.7 |

FIG. 3

FAVS-1-ENV after 20 hours

FAVS-2-ENV after 20 hours

FAVS-3-ENV after 20 hours

FIG. 4

ANTIGEN DELIVERY VECTORS AND CONSTRUCTS

CROSS-REFERENCE TO RELATED APPLICATIONS

This application is a continuation of U.S. application Ser. No. 13/354,871, filed Jan. 20, 2012, which is a continuation of U.S. application Ser. No. 12/700,526, filed Feb. 4, 2010, now U.S. Pat. No. 8,110,540, which is a continuation of U.S. patent application Ser. No. 11/096,725, filed Apr. 1, 2005, now U.S. Pat. No. 7,687,455, which claims the benefit of and priority to Great Britain Patent Application Serial No. 0408164.2, filed Apr. 13, 2004, the disclosures of each of which are incorporated herein by reference.

FIELD OF THE INVENTION

The present invention relates to novel antigen delivery constructs and their use in immunisation methods. In particular, the invention relates to constructs useful in immunising against human immunodeficiency virus.

BACKGROUND OF THE INVENTION

Recent advances in our comprehension of mammalian immunological responses have led to the prevention of certain diseases in man through prophylactic vaccination and the control and treatment of diseases by the use of immunotherapeutics. The types of diseases which may be addressed through immunological intervention include those caused by infectious agents, cancers, allergies and autoimmune diseases. In these cases, most commonly, the premise of the medical treatment is the efficient delivery of antigens to appropriate immune recognition cells. For example, prophylactic vaccination has successfully eradicated smallpox worldwide through the administration of a live attenuated strain of the virus bearing all the antigens of the wild type virus. Similarly infections due to the *Haemophilus influenzae* serotype b bacterium have been significantly reduced in Western countries following the development of a vaccine based upon the polysaccharide antigen from the bacterial cell wall. Moreover, some cancers such as human melanoma respond to immunotherapy using autologous dendritic cells (DC) as a cellular adjuvant and defined peptides derived from the melanosomal protein gp100 as the source of tumour-specific antigen to generate a cell-mediated immune response.

Self-tolerance to autoantigen can be restored in the treatment of experimental autoimmune encephalomyelitis by injection of a specific neuroantigen that is the target of the destructive immune response. Hence specificity can be afforded by such treatment without the need for long-term immunosuppression.

For infectious diseases, the most rapid progress in disease control has occurred where antibody raised to the administered antigen is capable of neutralising the infectious agent or toxin secreted therefrom, whether this be mediated through IgM, IgG or IgA. Likewise, autoimmune diseases have been treated with antigens that can ameliorate the action of auto-antibodies. However, for the eradication of virus-infected cells, cancer cells and cells harbouring intracellular bacteria, cellular immune responses are also required. For example, intracellular viruses (e.g. retroviruses, oncornaviruses, orthomyxoviruses, paramyxoviruses, togaviruses, rhabdoviruses, arenaviruses, adenoviruses, herpesviruses, poxviruses, papovaviruses and rubella viruses) are able to replicate and spread to adjacent cells without becoming exposed to antibody. The importance of cell-mediated immunity is emphasised by the inability of children with primary T-cell deficiency to clear these viruses, whilst patients with immunoglobulin deficiency but intact cell-mediated immunity do not suffer this handicap. A small, but important, number of bacteria, fungi, protozoa and parasites survive and replicate inside host cells. These organisms include *Mycobacteria* (tuberculosis and leprosy), *Legionella* (Legionnaires Disease), Rickettsiae (Rocky Mountain spotted fever), Chlamydiae, *Listeria monocytogenes, Brucella, Toxoplasma gondii, Leishmania, Trypanosoma, Candida albicans, Cryptococcus, Rhodotorula* and *Pneumocystis*. By living inside cells, these organisms are inaccessible to circulating antibodies. Innate immune responses are also ineffective. The major immune defense against these organisms is cell-mediated immunity; involving both CD8+ cytolytic T Lymphocytes and CD4 helper T Lymphocytes.

The development of vaccines and immunotherapeutics capable of eliciting an effective and sustained cell-mediated immune response remains one of the greatest challenges in vaccinology. In particular the development of a safe and efficacious vaccine for the prevention and treatment of Human Immunodeficiency Virus (HIV) infection has been hindered by the inability of vaccine candidates to stimulate robust, durable and disease-relevant cellular immunity.

The host cell-mediated immune response responsible for eradicating intracellular pathogens or cancer cells is termed the Th1 response. This is characterised by the induction of cytotoxic T-lymphocytes (CTL) and T-helper lymphocytes (HTL) leading to the activation of immune effector mechanisms as well as immunostimulatory cytokines such as IFN-gamma and IL-2. The importance of Th 1 responses in the control of viral infection has recently been shown by Lu et al. (Nature Medicine (2004)). This clinical study with chronically HIV-1 infected individuals demonstrated a positive correlation between the suppression of viral load and both the HIV-1-specific IL-2- or IFN-gamma-expressing CD4+ T cells and specific HIV-1 CD8+ effector cell responses. Current immunological strategies to improve the cellular immunity induced by vaccines and immunotherapeutics include the development of live attenuated versions of the pathogen and the use of live vectors to deliver appropriate antigens or DNA coding for such antigens. Such approaches are limited by safety considerations within an increasingly stringent regulatory environment. Furthermore, issues arising from the scalability of manufacturing processes and cost often limit the commercial viability of products of biological origin.

In this context, rationally defined synthetic vaccines based on the use of peptides have received considerable attention as potential candidates for the development of novel prophylactic vaccines and immunotherapeutics. T cell and B cell epitopes represent the only active part of an immunogen that are recognized by the adaptive immune system. Small peptides covering T or B cell epitope regions can be used as immunogens to induce an immune response that is ultimately cross-reactive with the native antigen from which the sequence was derived. Peptides are very attractive antigens as they are chemically well-defined, highly stable and can be designed to contain T and B cell epitopes. T cell epitopes, including CTL and T helper epitopes, can be selected on the basis of their ability to bind MHC molecules in such a way that broad population coverage can be achieved (The HLA Factsbook, Marsh, S., Academic Press. 2000). Moreover, the ability to select appropriate T and B cell epitopes enable the immune response to be directed to multiple conserved epitopes of pathogens which are characterised by high sequence variability (such as HIV, hepatitis C virus (HCV), and malaria).

In order to stimulate T lymphocyte responses, synthetic peptides contained in a vaccine or an immunotherapeutic product should preferably be internalized by antigen presenting cells and especially dendritic cells. Dendritic cells (DCs) play a crucial role in the initiation of primary T-cell mediated immune responses. These cells exist in two major stages of maturation associated with different functions. Immature dendritic cells (iDCs) are located in most tissues or in the circulation and are recruited into inflamed sites. They are highly specialised antigen-capturing cells, expressing large amounts of receptors involved in antigen uptake and phagocytosis. Following antigen capture and processing, iDCs move to local T-cell locations in the lymph nodes or spleen. During this process, DCs lose their antigen-capturing capacity turning into immunostimulatory mature Dcs (mDCs).

Dendritic cells are efficient presenting cells that initiate the host's immune response to peptide antigen associated with class I and class II MHC molecules. They are able to prime naïve CD4 and CD8 T-cells. According to current models of antigen processing and presentation pathways, exogenous antigens are internalised into the endocytic compartments of antigen presenting cells where they are degraded into peptides, some of which bind to MHC class II molecules. The mature MHC class II/peptide complexes are then transported to the cell surface for presentation to CD4 T-lymphocytes. In contrast, endogenous antigen is degraded in the cytoplasm by the action of the proteosome before being transported into the cytoplasm where they bind to nascent MHC class I molecules. Stable MHC class I molecules complexed to peptides are then transported to the cell surface to stimulate CD8 CTL. Exogenous antigen may also be presented on MHC class I molecules by professional APCs in a process called cross-presentation. Phagosomes containing extracellular antigen may fuse with reticulum endoplasmic and antigen may gain the machinery necessary to load peptide onto MHC class I molecules. It is well recognised, however, that free peptides are often poor immunogens on their own (Fields Virology, Volume 1, Third Edition, 1996).

To optimise the efficacy of peptide vaccines or therapeutics, various vaccine strategies have been developed to direct the antigens into the antigen-presenting cell in order to target the MHC class I pathway and to elicit cytotoxic T-lymphocyte (CTL) responses. As an example of a synthetic delivery system, fatty acyl chains have been covalently to linked to peptides as a means of delivering an epitope into the MHC class I intracellular compartment in order to induce CTL activity. Such lipopeptides, for example with a monopalmitoyl chain linked to a peptide representing an epitope from HIV Env protein are described in the U.S. Pat. No. 5,871, 746. Other technologies have been delivered that aim to deliver epitopes into the intracellular compartment and thereby induce CTLs. These include vectors such as Penetratin, TAT and its derivatives, DNA, viral vectors, virosomes and liposomes. However, these systems either elicit very weak CTL responses, have associated toxicity issues or are complicated and expensive to manufacture at the commercial scale.

There is therefore a recognised need for improved vectors to direct the intracellular delivery of antigens in the development of vaccines and drugs intended to elicit a cellular immune response. A vector in the context of immunotherapeutics or vaccines is any agent capable of transporting or directing an antigen to immune responsive cells in a host. Fluorinated surfactants have been shown to have lower critical micellar concentrations than their hydrogenated counterparts and thus self-organise into micelle structures at a lower concentration than the equivalent hydrocarbon molecule. This physicochemical property is related to the strong hydrophobic interactions and low Van der Waal's interactions associated with fluorinated chains which dramatically increase the tendency of fluorinated amphiphiles to self-assemble in water and to collect at interfaces. The formation of such macromolecular structures facilitates their endocytic uptake by cells, for example antigen-presenting cells (Reichel F. et al. *J. Am. Chem. Soc.* 1999, 121, 7989-7997). Furthermore haemolytic activity is strongly reduced and often suppressed when fluorinated chains are introduced into a surfactant (Riess, J. G.; Pace, S.; Zarif, L. *Adv. Mater.* 1991, 3, 249-251) thereby leading to a reduction in cellular toxicity.

SUMMARY OF THE INVENTION

This invention seeks to overcome the problem of delivering antigens to immune responsive cells by using a novel fluorocarbon vector in order to enhance the immunogenicity of administered antigens. The fluorocarbon vector may comprise one or more chains derived from perfluorocarbon or mixed fluorocarbon/hydrocarbon radicals, and may be saturated or unsaturated, each chain having from 3 to 30 carbon atoms. In order to link the vector to the antigen through a covalent linkage, a reactive group, or ligand, is incorporated as a component of the vector, for example —CO—, —NH—, S, O or any other suitable group is included; the use of such ligands for achieving covalent linkages are well-known in the art. The reactive group may be located at any position on the fluorocarbon molecule. Coupling of the fluorocarbon vector to the antigen may be achieved through functional groups such as —OH, —SH, —COOH, $—NH_2$ naturally present or introduced onto any site of the antigen. Examples of such linkages include amide, hydrazone, disulphide, thioether and oxime bonds. Alternatively, non-covalent linkages can be used, for example an ionic interaction may be formed via a cation linking together a histidine residue of a peptide antigen and a carboxylic acid on the fluorocarbon vector. Optionally, a spacer element (peptidic or non-peptidic) may be incorporated to permit cleavage of the antigen from the fluorocarbon element for processing within the antigen-presenting cell and to optimise steric presentation of the antigen. The spacer may also be incorporated to assist in the synthesis of the molecule and to improve its stability and/or solubility. Examples of spacers include polyethylene glycol (PEG), amino acids such as lysine or arginine that may be cleaved by proteolytic enzymes and hydrocarbons.

Thus, in a first aspect, the present invention provides a fluorocarbon vector having a chemical structure or derivatives thereof, where m=3 to 30, n<=2m+1, y=0 to 15, x<=2y, (m+y)=3 −30 and L is a ligand to facilitate covalent attachment to an antigen.

In the context of the present invention "derivatives" refers to relatively minor modifications of the fluorocarbon compound such that the compound is still capable of delivering the antigen as described herein. Thus, for example, a number of the fluorine moieties can be replaced with other halogen moieties such as Cl, Br or I. In addition it is possible to replace a number of the fluorine moieties with methyl groups and still retain the properties of the molecule as discussed herein.

In a particular embodiment of the above formula the vector may be perfluoroundecanoic acid of the following formula (I):

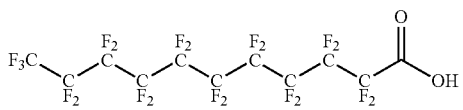 [SMILES: O=C(O)C(F)(F)C(F)(F)C(F)(F)C(F)(F)C(F)(F)C(F)(F)C(F)(F)C(F)(F)C(F)(F)C(F)(F)F]

or alternatively 2H, 2H, 3H, 3H-perfluoroundecanoic acid of the following formula (II):

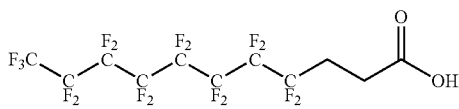

or heptadecafluoro-pentadecanoic acid of the following formula (III):

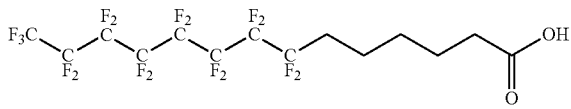 [SMILES: O=C(O)CCCCCC(F)(F)C(F)(F)C(F)(F)C(F)(F)C(F)(F)C(F)(F)C(F)(F)C(F)(F)F]

In a second aspect the invention provides a vector-antigen construct $C_mF_n$-$C_yH_x$-(Sp)-R where Sp is an optional chemical spacer moiety and R is an antigen.

The antigen associated with the vector may be any antigen capable of inducing an immune response in an animal, including humans Preferably the immune response will have a beneficial effect in the host. Antigens may be derived from a virus, bacterium or mycobacterium, parasite, fungus, or any infectious agent or an autologous antigen or allergen.

Examples of viruses include, but are not limited to, Human Immunodeficiency Virus-1 (HIV-1) or -2, influenza virus, Herpes virus HSV-1 and HSV-2), hepatitis A virus (HAV), hepatitis B virus (HBV), or hepatitis C virus (HCV).

Examples of bacteria and mycobacteria include, but are not limited to *Mycobacterium tuberculosis, Legionella, Rickettsiae, Chlamydiae,* and *Listeria monocytogenes.*

Examples of parasites include, but are not limited to *Plasmodium falciparum* and other species of the Plasmodial family.

Examples of fungi include, but are not limited to *Candida albicans, Cryptococcus, Rhodotorula* and *Pneumocystis.*

Autologous or self-antigens include, but are not limited to the following antigens associated with cancers, HER-2/neu expressed in breast cancer, gp 100 or MAGE-3 expressed in melanoma, P53 expressed in colorectal cancer, and NY-ESO-1 or LAGE-1 expressed by many human cancers.

Allergens include, but are not limited to. phospholipase A₂ (API ml) associated with severe reactions to bee, Derp-2, Der p 2, Der f, Der p 5 and Der p 7 associated with reaction against the house-dust mite *Dermatophagoides pteronyssinus,* the cockroach allergen Bla g 2 and the major birch pollen allergen Bet v 1.

Thus in a embodiment, the present invention provides a vector-antigen construct where the antigen is, or represents, an antigen from a virus, bacterium, mycobacterium, parasite, fungus, autologous protein or allergen.

Antigens may be proteins, protein subunits, peptides, carbohydrates, lipid or combinations thereof, provided they present an immunologically recognisable epitope. Such antigens may be derived by purification from the native protein or produced by recombinant technology or by chemical synthesis. Methods for the preparation of antigens are well-known in the art. Furthermore antigens also include DNA or oligonucleotide encoding an antigenic peptide or protein.

Thus in yet a further embodiment, the present invention provides a vector-antigen construct where the antigen is a protein, protein subunit, peptide, carbohydrate or lipid or combinations thereof.

For the construct to be immunologically active the antigen must comprise one or more epitopes. Peptides or proteins used in the present invention preferably contain a sequence of at least seven, more preferably between 9 and 100 amino-acids and most preferably between around 15 to 35 amino acids. Preferably, the amino acid sequence of the epitope(s) bearing peptide is selected to enhance the solubility of the molecule in aqueous solvents. Furthermore, the terminus of the peptide which does not conjugate to the vector may be altered to promote solubility of the construct via the formation of multimolecular structures such as micelles, lamellae, tubules or liposomes. For example, a positively charged amino acid could be added to the peptide in order to promote the spontaneous assembly of micelles. Either the N-terminus or the C-terminus of the peptide can be coupled to the vector to create the construct. To facilitate large scale synthesis of the construct, the N- or C-terminal amino acid residues of the peptide can be modified. When the desired peptide is particularly sensitive to cleavage by peptidases, the normal peptide bond can be replaced by a noncleavable peptide mimetic; such bonds and methods of synthesis are well known in the art.

As a specific example, the peptide NNTRKRIRIQRGPGRAFVTIGK-$NH_2$ (SEQ ID NO: 37) represents an epitope from the Env (301-322) protein of HIV-1, which has been shown to be immunologically active. This represents yet another embodiment of the present invention. (Reference http://www.hiv.lanl.gov/content/immunology/index.html).

More than one antigen may be linked together prior to attachment to the ligand. One such example is the use of fusion peptides where a promiscuous T helper epitope can be covalently linked to one or multiple CTL epitopes or one or multiple B cell epitope which can be a peptide, a carbohydrate, or a nucleic acid. As an example, the promiscuous T helper epitope could be the PADRE peptide, tetanus toxoid peptide (830-843) or influenza haemagglutinin, HA (307-319).

In another embodiment therefore, the vector-antigen construct is one where R is more than one epitope or antigen linked together. Epitopes may also be linear overlapping thereby creating a cluster of densely packed multi-specific epitopes.

Due to the strong non-covalent molecular interactions characteristic to fluorocarbons, the antigen may also be non-covalently associated with the vector and still achieve the aim of being favourably taken up by antigen-presenting cells The present invention also provides vaccines and immunotherapeutics comprising one or more fluorocarbon vector-antigen constructs. Multi-component products of this type are desirable since they are likely to be more effective in eliciting appropriate immune responses. For example, the optimal formulation of an HIV immunotherapeutic may comprise a number of epitopes from different HIV proteins. In this case each epitope may be linked to a common fluorocarbon vector or each epitope could be bound to a dedicated vector. Alternatively, multiple epitopes may be incorporated into a formulation in order to confer immunity against a range of pathogens. A multi-component product may contain one or more vector-antigen construct, more preferably 2 to about 20, more preferably 3 to about 8 such constructs.

Compositions of the invention comprise fluorocarbon vectors associated to antigens optionally together with one or more pharmaceutically acceptable carriers and/or adjuvants. Such adjuvants, capable of further potentiating the immune response, may include, but are not limited to, muramyldipeptide (MDP) derivatives, CpG, monophosphoryl lipid A, oil in water adjuvants, water-in-oil adjuvants, aluminium salts, cytokines, immunostimulating complex (ISCOMs), liposomes, microparticules, saponins, cytokines, or bacterial toxins and toxoids. Other useful adjuvants will be well-known to one skilled in the art. The choice of carrier if required is frequently a function of the route of delivery of the composition. Within this invention, compositions may be formulated for any suitable route and means of administration. Pharmaceutically acceptable carriers or diluents include those used in formulations suitable for oral, ocular, rectal, nasal, topical (including buccal and sublingual), vaginal or parenteral (including subcutaneous, intramuscular, intravenous, intradermal) administration.

The formulation may be administered in any suitable form, for example as a liquid, solid, aerosol, or gas. For example, oral formulations may take the form of emulsions, syrups or solutions or tablets or capsules, which may be enterically coated to protect the active component from degradation in the stomach. Nasal formulations may be sprays or solutions. Transdermal formulations may be adapted for their particular delivery system and may comprise patches. Formulations for injection may be solutions or suspensions in distilled water or another pharmaceutically acceptable solvent or suspending agent. Thus in a further aspect, the present invention provides a prophylactic or therapeutic formulation comprising the vector-antigen construct with or without a suitable carrier and/or adjuvant.

The appropriate dosage of the vaccine or immunotherapeutic to be administered to a patient will be determined in the clinic. However, as a guide, a suitable human dose, which may be dependent upon the preferred route of administration, may be from 1 to 1000 µg. Multiple doses may be required to achieve an immunological effect, which, if required, will be typically administered between 2 to 12 weeks apart. Where boosting of the immune response over longer periods is required, repeat doses 3 months to 5 years apart may be applied.

The formulation may combine the vector-antigen construct with another active component to effect the administration of more than one vaccine or drug. A synergistic effect may also be observed through the co-administration of the two or more actives. In the treatment of HIV infection, an example of one such drug is Highly Active Anti-Retroviral Therapy (HAART).

In other aspects the invention provides:
i) Use of the immunogenic construct as described herein in the preparation of a medicament for treatment or prevention of a disease or symptoms thereof.
ii) A method of treatment through the induction of an immune response following administration of the constructs or formulations described herein;
iii) The use of the fluorocarbon vectors and fluorocarbon vector-antigen constructs in medicine.

BRIEF DESCRIPTION OF THE DRAWINGS

The examples refer to the figures in which:
FIG. 3: shows critical micelle concentration evaluation for two peptides, FAVS-3-ENV and FAVS-1-ENV;
FIG. 4: shows particle size analysis by quasi light scattering spectrometry after 20 hours standing for various peptide constructs.

DETAILED DESCRIPTION

Example 1

Synthesis of Fluorocarbon-Vectored Peptides

The following fluorocarbon-vector peptides were synthesised:

FAVS-1-ENV:
(SEQ ID NO: 38)
NNTRKRIRIQRGPGRAFVTIGK-$C_8F_{17}(CH_2)_2$CO-K-$NH_2$

FAVS-2-ENV:
(SEQ ID NO: 38)
NNTRKRIRIQRGPGRAFVTIGK-$C_8F_{17}(CH_2)_6$CO-K-$NH_2$

FAVS-3-ENV:
(SEQ ID NO: 39)
IRIQRGPGRAFVTIGKK-CO$(CH_2)_2$-(PEG)$_4$-$C_8F_{17}(CH_2)_6$CO-K-$NH_2$

Where the standard amino acid one letter code is utilised and PEG is $CH_2$-$CH_2$-O. NNTRKRIRIQRGPGRAFVTIGK (SEQ ID NO: 37) is the ENV(301-322) peptide of the Human Immunodeficiency Virus.

Peptide synthesis was carried out on an ABI 430 or ABI 433 automatic peptide synthesizer, on Rink amide resin (0.38 mmol/g loading) using Nsc (2-(4-nitrophenylsulfonyl) ethoxycarbonyl), or Fmoc ((9-fluorenylmethylcarbonyl) amino acids. Coupling was promoted with HOCt (6-Chloro-1-oxybenzotriazole) and DIC (1,3-diisopropylcarbodiimide), and Fmoc/Nsc deprotection was carried out using 20% piperidine in DMF (Dimethylformamide). Uncoupled N-termini were capped with acetic anhydride as part of each cycle. Cleavage of the peptide from resin and concomitant side-chain deprotection was achieved using TFA, water and TIS (Diisopropylsilane) (95:3:2), with crude isolation of product by precipitation into cold diethyl ether. Purification was performed by preparative HPLC using Jupiter C5 or Luna C18 (2) columns (250×22 mm) and peptide mass was verified by mass spectrometry.

Peptide purity was verified prior to conducting the experiments by HPLC(HP 1050) using a column from Supelco (C5, 250×4.6 mm, 300 A, 5 μm) under gradient elution. Solvent A (90% Water, 10% Acetonitrile, 0.1% TFA), Solvent B (10% Water, 90% Acetonitrile, 0.1% TFA). A gradient 0 to 100% of B in 30 minutes was used and column temperature was 40° C. The wavelength of the UV detector was set up at 215 nm. Purity of the fluorocarbon-vector peptides in each case was greater than 90%.

Figure 1:
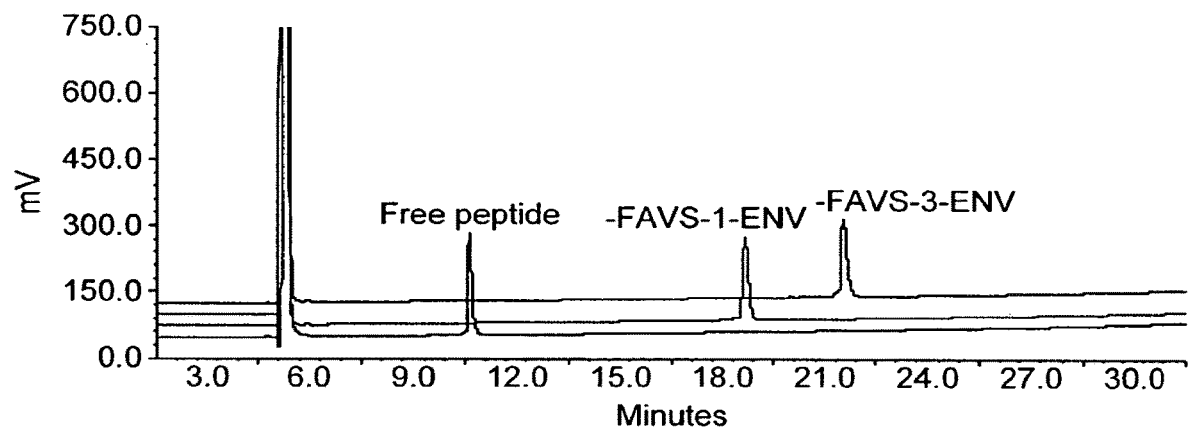
FIG. 1: shows HPLC chromatograms of various peptides and constructs at T=0.
Figure 2:
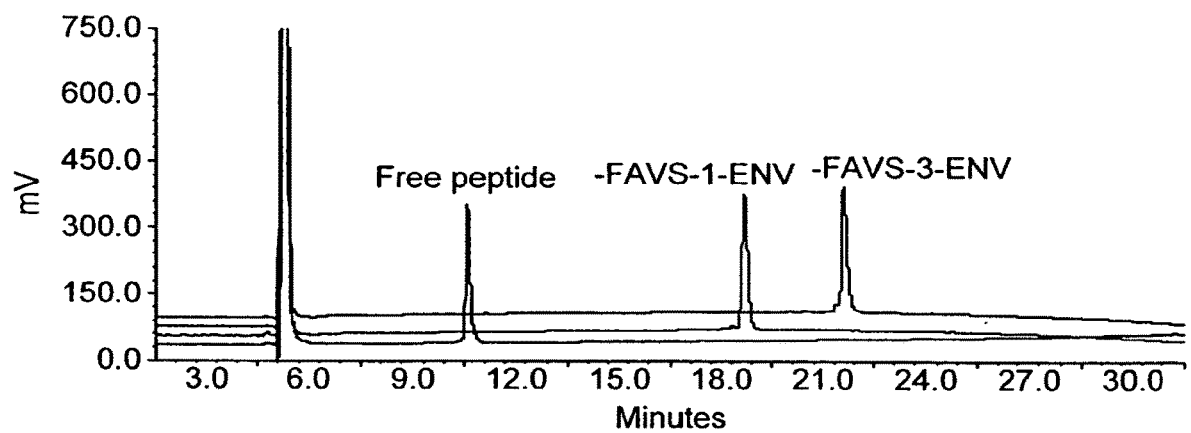
FIG. 2: shows HPLC chromatograms of various peptides and constructs stored at 40° C. for 27 days.

The chemical stability of hermetically sealed samples containing lyophilised vector-peptides was assessed at 4° C., 20° C. and 40° C. together with the unvectored peptide as a comparator (NNTRKRIRIQRGPGRAFVTIGK-NH$_2$ (SEQ ID NO: 37)). The stability over the time was monitored by HPLC using the conditions described above. The data is shown in FIGS. 1 and 2.

For each peptide conjugate, no sign of degradation was observed after 27 days at 40° C. incubation, with a single peak eluting at the same retention time as found at T=0.

Example 2

Physicochemical analysis of Fluorocarbon-vectored peptides
(i) Solubility

The solubility of the fluorocarbon-vector peptides in aqueous solution at concentrations useful for a pharmaceutical formulation was confirmed. Solutions of peptides were prepared at 20° C. by dissolving the lyophilised peptide powder with PBS (0.01M, pH 7.2) across a range of concentrations. Preparations were then vortexed for one minute. An aliquot was collected and the remainder of the solution was centrifuged for 10 minutes at 12,000 rpm. To a 96-well flat bottom plate containing 25 μl aliquots of serial dilutions of each peptide was added 200 μl of the BCA working reagent (Pierce, UK) containing the solution A (bicichoninic acid, sodium carbonate, sodium tartrate in a sodium hydroxide 0.1M solution, 50 vol,) and B (4% cupric sulphate solution, 1 vol.). After incubating for 45 minutes at 37° C. and cooling for 10 minutes, the absorbance was measured at 570 nm. The plates were analysed by a Wallac Victor multilabel counter (Perkin Elmer). For each peptide a calibration curve was plotted and used to determine the peptide concentration in the soluble fraction, expressed in nmol/ml. Data are presented Table 1. All the peptides were found to be fully soluble at the concentration of antigen used for murine immunisation studies.

TABLE 1

Summary of the solubility assay performed by the protein assay method

| Peptide | Solubility |
| --- | --- |
| Free peptide | >3300 nmol/ml |
| FAVS-1-ENV | >4000 nmol/ml |
| FAVS-2-ENV | >500 nmol/ml |
| FAVS-3-ENV | >3000 nmol/ml |

(ii) Critical Micelle Concentration [CMC]

The Critical Micelle Concentration of the fluorocarbon-vectored peptides in physiological phosphate buffered saline was determined by dye bonding with 8-anilino-1-naphthalene-sulphonic acid (ANS). Starting from 300 μg peptide/ml solutions, serial two-fold dilutions of the peptide and peptide-vector solutions in PBS (0.01M, pH 7.2) were prepared at 20° C., from which 200 μl were added to the wells of a microplate. 40 μl of freshly dissolved ANS in PBS was then added to each well. After two minutes the plate was excited at 355 nm and scanned at 460 nm on a Victor microplate fluorimeter. The ratio (Intensity of fluorescence of the sample/Intensity of fluorescence of the blank) was plotted on a linear scale versus the concentration on a logarithmic scale. Data are presented FIG. 3.

(iii) Particle Size Analysis

Particle size analysis was performed on a Malvern 4700C Quasi Light Scattering spectrometer (Malvern Ltd, UK) equipped with an Argon laser (Uniphase Corp., San Jose, Calif.) tuned at 488 nm. Samples were maintained at a temperature of 25° C. The laser has variable detector geometry for angular dependence measurement. Measurements were performed at angles of 90° and 60°. Solutions were prepared by dissolving the peptide in filtered 0.01M phosphate buffered saline to a concentration of 500 nmol/ml and vortexing for 1 minute. Solutions were then dispensed into cuvettes (working volume of 1 ml). Measurements were taken after 15 minutes at an angle of 90° (FIG. 4). The Kcount value output is proportional to the number of particles detected; in all cases the Kcount was >10 in order to ensure that reliable size distribution measurements were obtained.

TABLE 2

Particle size of micellar solution in PBS.

| ITS reference | Standing Time (h) | Kcount | size (nm) Population1 | size (nm) Population2 | Average size (nm) | Polydispersity |
| --- | --- | --- | --- | --- | --- | --- |
| FAVS-1-ENV | 0.25 | 177 | 28 | — | 28.3 | 0.151 |
|  | 20 | 230 | 32 | — | 32.7 | 0.180 |
| FAVS-2-ENV | 0.25 | 190 | 15 | 120 | 28.5 | 0.450 |
|  | 20 | 245 | 20 | 300 | 68.4 | 0.539 |
| FAVS-3-ENV | 0.25 | 201 | 70 | 400 | 209 | 0.659 |
|  | 20 | 225 | 105 | 800 | 207 | 0.647 |

Example 3

(i) Immunogenicity of Fluorocarbon-Vectored Peptides

Specific-pathogen-free mice (6-8 week female Balb/c) were purchased from Harlan (UK). Peptides ENV, FAVS-1-ENV, FAVS-2-ENV or FAVS-3-ENV were dissolved in PBS (0.01M, pH 7.2). Each dose was normalised to 50 nmol peptide per ml based on the net peptide content obtained from amino-acid analysis. Mice (3 per group) were immunized subcutaneously under the skin of the interscapular area with 50 nmol peptide in a volume of 100 µl PBS, pH 7.2. Three doses were administered at ten day intervals. A mouse group receiving a priming dose of free peptide admixed with Complete Freund's adjuvant (50 nmol peptide in PBS emulsified in an equal volume of adjuvant) and booster doses of Incomplete Freund's adjuvant served as a positive control. Ten days after the final immunisation mice were sacrificed and spleens removed to assess the cellular immune response to the peptide. To determine the progress of the immune response development, groups of mice receiving a single and two doses of peptide were also set up.

The in vivo cellular response primed by the vectored peptides was monitored by IFN-gamma ELISPOT on fresh spleen cells in order to enumerate the ex-vivo frequency of peptide-specific IFN-gamma producing cells and more specifically peptide-specific CD8+T lymphocytes primed following immunisation. Spleen cells were restimulated in vitro with the ENV(301-322) NNTRKRIRIQRGPGRAFVTIGK (SEQ ID NO: 37) peptide containing a well-known T-helper epitope and ENV (311-320) RGPGRAFVTI (SEQ ID NO: 40) a shorter peptide corresponding to the CD8 epitope (MHC class I H-2Dd-restricted known as P18-I10) in order to cover both components of the cellular immune response (T Helper and CD8 T cell activity).

The spleens from each group of mice were pooled and spleen cells isolated. Cells were washed three times in RPMI-1640 before counting. Murine IFN-g Elispot assays were performed using Diaclone Kit (Diaclone, France) according to the manufacturer's instructions with the following modifications. Duplicate culture of spleen cells at cell density of $5 \times 10^5$/well were distributed in anti-IFN-gamma antibody coated PVDF bottomed-wells (96-well multiscreen™-IP microplate-Millipore) with the appropriate concentration of peptide (10µ, 1, 0 mg/ml of T helper EN-(301-322) or P18-I10 CTL epitope) in culture medium (RPMI-1640), 5 µM β-mercaptoethanol, 5 mM glutamine supplemented with 10% Foetal Calf Serum during 18 hours at 37° C. under 5% $CO_2$ atmosphere. The spots were counted using a Carl Zeiss Vision ELIspot reader unit. The results correspond to mean values obtained with each conditions after background subtraction. Results are expressed as spot forming units (SFC) per million input spleen cells (FIG. 5).

(ii) Nature of T Lymphocytes Primed in vivo by the Fluorocarbon-Peptides (CD4 and CD8 T Cell Separation)

Spleen Cells from immunized mice were distributed in 48-well microplates at cell density of $2.5 \times 10^6$/well with 1 µg/ml of T helper ENV(301-322) or P18-I10 CTL peptides. At day 3, 5 ng/ml of recombinant murine IL-2 was added to each well. At day 7, pre-stimulated spleen cells were harvested, washed three times in RPMI 1640, counted and separated by magnetic cell sorting using magnetic beads conjugated with monoclonal rat anti-mouse CD8a and CD4 antibodies (MACS, Microbeads Miltenyi Biotec, UK) according to manufacturer's instructions. CD4 and CD8+ T cells were distributed at cell density of $2.5 \times 10^5$/well in duplicate in antibody coated PVDF bottomed-wells (96-well multiscreen™-IP microplate, Millipore) with 1 mg/ml of peptide in culture medium (RPMI-1640, 5 µM β-mercaptoethanol, Glutamine, non-essential amino-acids, sodium pyruvate supplemented with 10% Foetal Calf Serum for 12 hours at 37° C. under 5% $CO_2$ atmosphere. The spots were counted using a Carl Zeiss Vision ELIspot reader unit. The results correspond to mean values obtained with each conditions after background subtraction (<10 spots). Results are expressed as spot forming units (SFC) per million input spleen cells.

Figure 5:
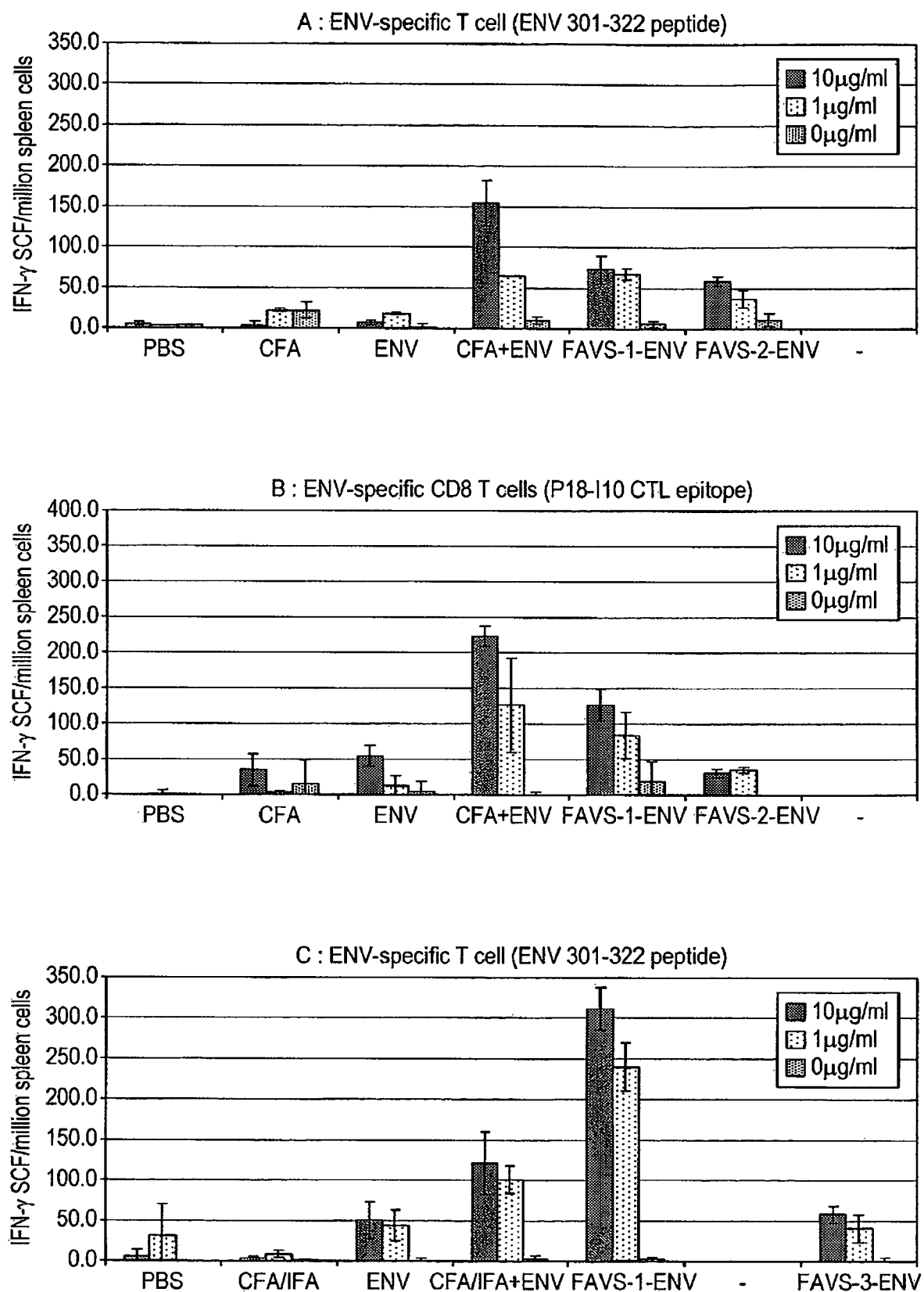
FIG. 5: shows cellular immune response assessed by ex vivo IFN-gamma ELISPOT assay in mice after single immunisation (A,B), first boost (C,D) and second boost (E,F)
Figure 5:
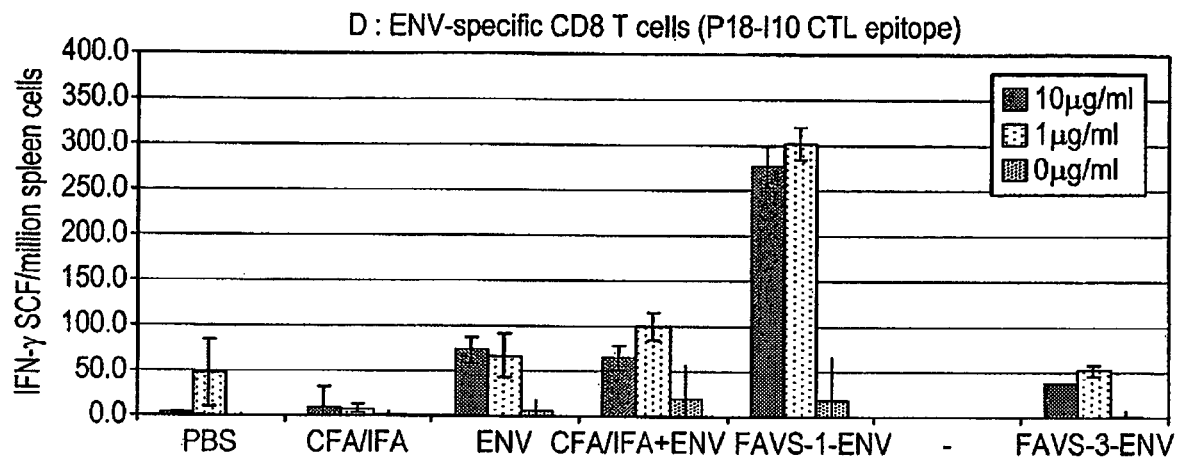
Figure 5:
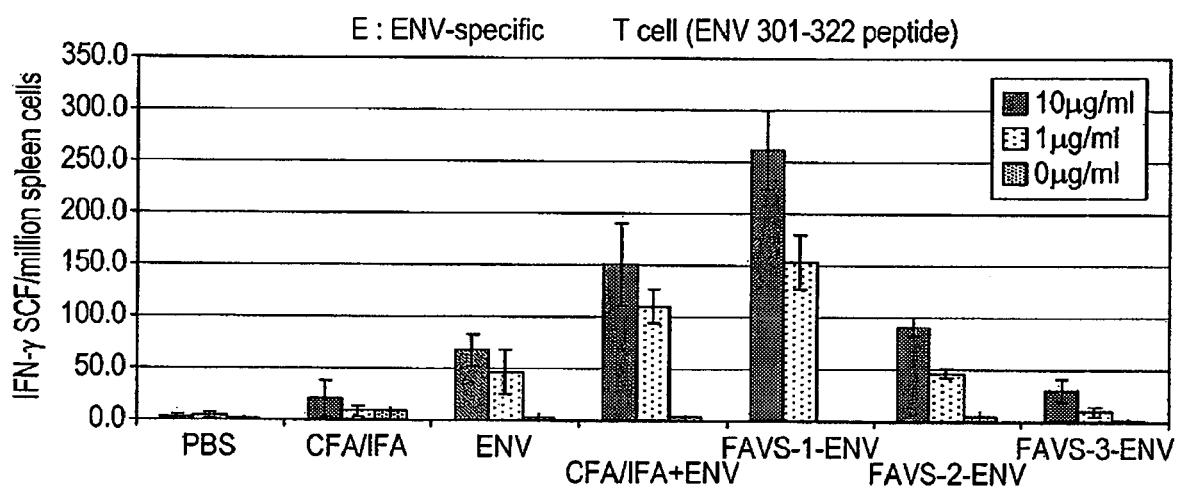
Figure 5:
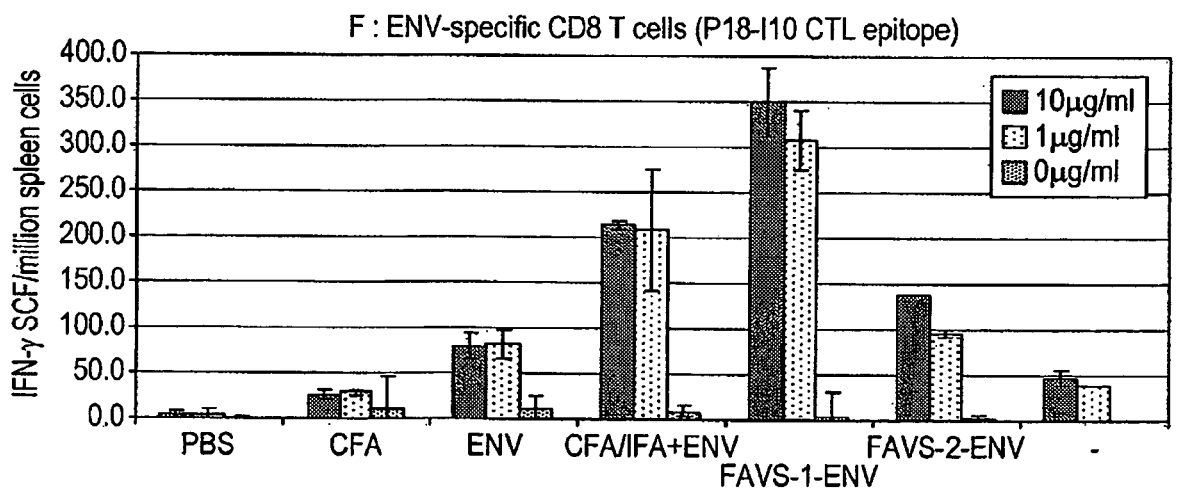
Figure 6:
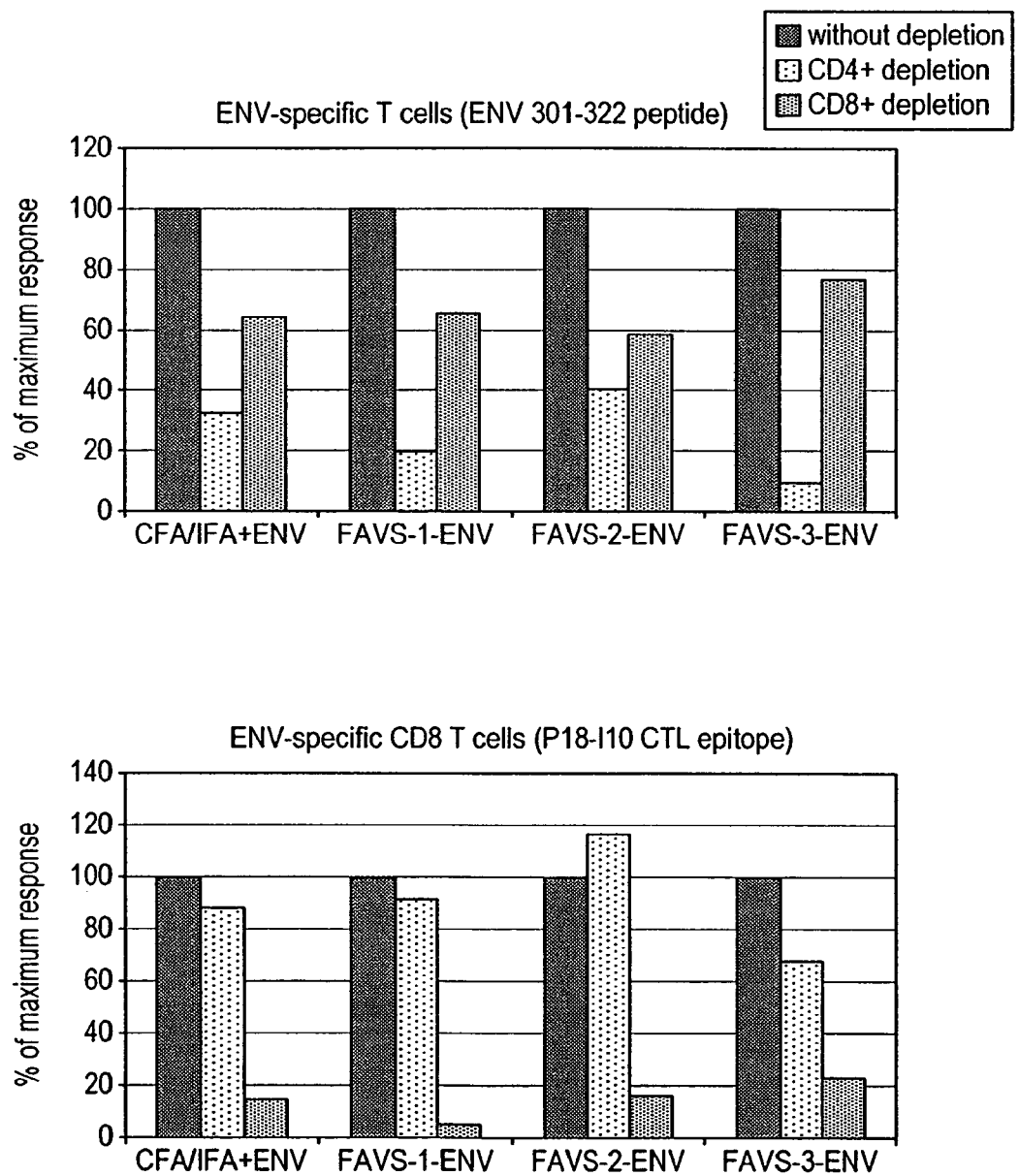
FIG. 6 shows nature of T lymphocytes primed in vivo by various fluorocarbon-peptide constructs.

According to the ex vivo IFN-γ ELISPOT assays, the FAVS-peptide constructs were able to prime a strong cellular immune response against both the long (ENV301-322) and the short ENV peptides (P18-I10 CTL epitope) after a single in vivo exposure to the antigen (FIGS. 5 A and B). FIG. 6 demonstrates that both CD4+ and CD8+ ENV-specific T cells were efficiently primed in vivo.

The intensity of the response after priming with the FAVS-peptides was in the same range as the responses obtained from mice immunized with the native peptide emulsified in Freund's adjuvant. ENV-specific T cell responses are clearly amplified after a first and a second boost with the FAVS-1-ENV formulation (FIG. 5C, D, E, F) as summarized in FIG. 6.

This clearly demonstrates the ability of the FAVS-peptides to be taken up by antigen presenting cells in vivo in order to reach the MHC class I and MHC class II pathways and thereby prime strong cellular immune responses.

Example 4

Immunogenicity of Fluorocarbon-Vectored Peptides Co-Administered with Synthetic Adjuvant In order to assess the potential impact of a synthetic immunostimulant on the quantitative and qualitative immunogenicity of the FAVS-peptides, FAVS-1-ENV was injected alone and in combination with Murabutide. Murabutide (N-acetyl-muramyl-L-alanyl-D-glutamine-O-n-butyl-ester; a synthetic derivative of muramyl dipeptide and NOD-2 agonist) is a synthetic immune potentiator that activates innate immune mechanisms and is known to enhance both cellular and humoral responses when combined with immunogens ("Immune and antiviral effects of the synthetic immunomodulator murabutide: Molecular basis and clinical potential", G. Bahr, in: "Vaccine adjuvants: Immunological and Clinical Principles", eds Hacket and Harn (2004), Humana Press).

Specific-pathogen-free mice (6-8 week female Balb/c) were purchased from Harlan (UK). The FAVS-1-ENV construct was used at two different dose levels, one group of mice receiving 50 nmoles and a second group received 5 nmoles of construct. Mice (3 per group) were immunized subcutaneously under the skin of the interscapular area with FAVS-1-ENV either alone or in combination with 100 µg of Murabutide in a total volume of 100 µl PBS, pH 7.2. Three doses were administered at ten day intervals. A control group receiving murabutide alone was also set up.

Figure 7:
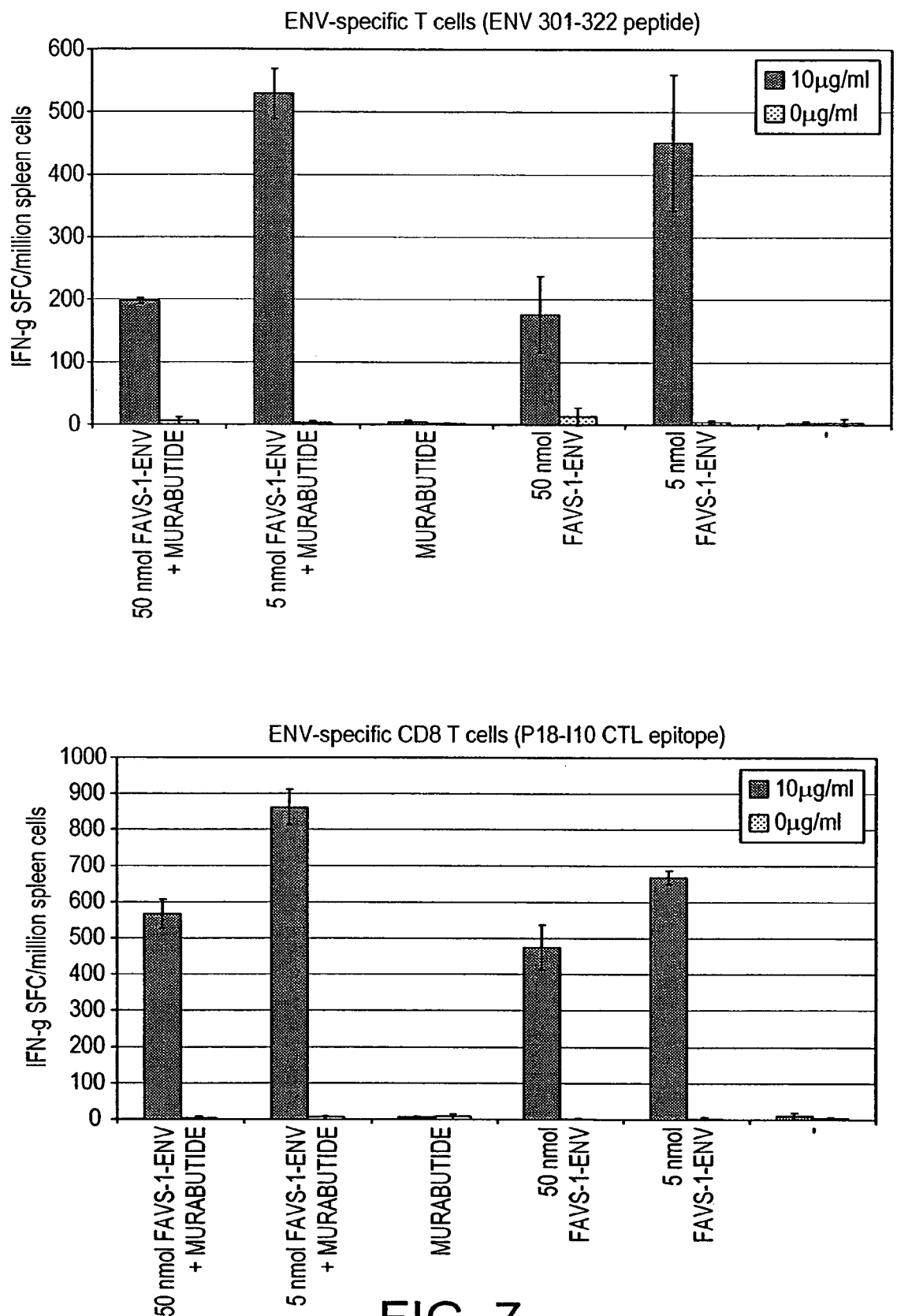
FIG. 7: shows cellular immune response assessed by ex vivo IFN-g ELISPOT assay in mice after three immunisations with FAVS-1-ENV alone or in combination with murabutide.

Ten days after the final immunisation mice were sacrificed and spleens removed to assess the cellular immune response to the T helper ENV(301-322) or P18-I10 CTL epitope peptides. Interferon-gamma Elispot and Th-1 and Th-2 cytokine measurements were performed on the isolated spleens as described in Example 3. Briefly, spleen cells were cultured with the appropriate concentration of peptide (10 or 0 µg/ml of T helper ENV (301-322) or P18-I10 CTL epitope) in culture medium during 18 hours at 37° C. under 5% $CO_2$ atmosphere. IFN-g Elispot assay was then performed. The spots were counted using a Carl Zeiss Vision Elispot reader unit. The results correspond to mean values obtained with each conditions after background subtraction (<10 spots). Results are expressed as spot forming units (SFC) per million input spleen cells (FIG. 7).

Multiplex cytokine measurements (IL-2, IFN-g, IL4, IL5, IL-10, IL-13) were performed on fresh spleen cells re-stimulated with the ENV (301-322) peptide from mice immunised with the 5 nmol dose of FAVS-1-ENV. Supernatants were collected at 24 hours and 48 hours. Levels of cytokines (IL2, IL4, IL-5, IL-10, IL-13, IFN-γ) in cell culture supernatant samples were measured using the Cytokine specific Sandwich ELISA according to the mutiplex format developed by SearchLight™ Proteomic Arrays (Pierce Biotechnology, Woburn, Mass.). Results were expressed in pg cytokine/ml.

Figure 8:
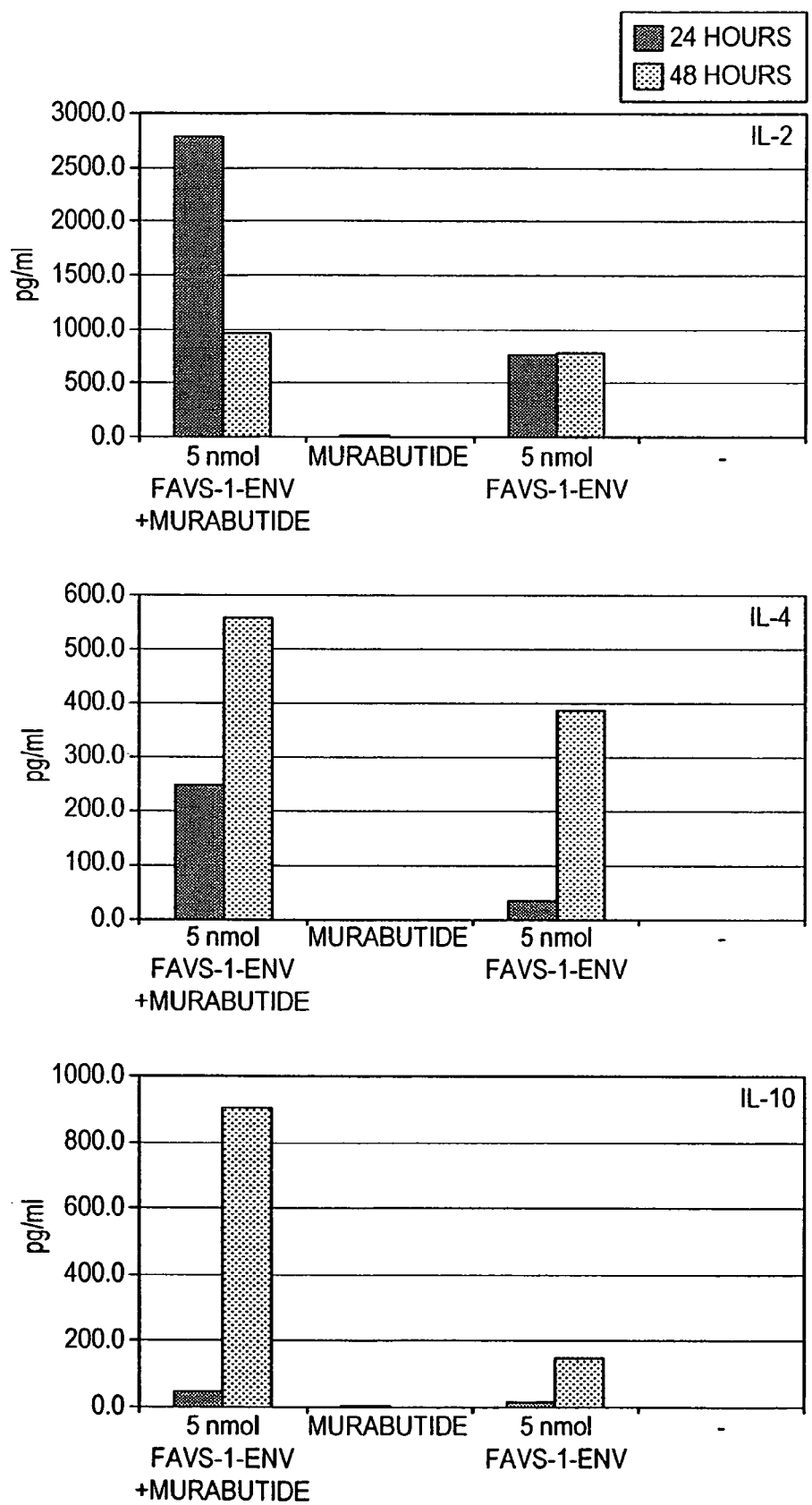
FIG. 8: cytokine measurement after three injections with FAVS-1-ENV alone or in combination with murabutide.
Figure 8:
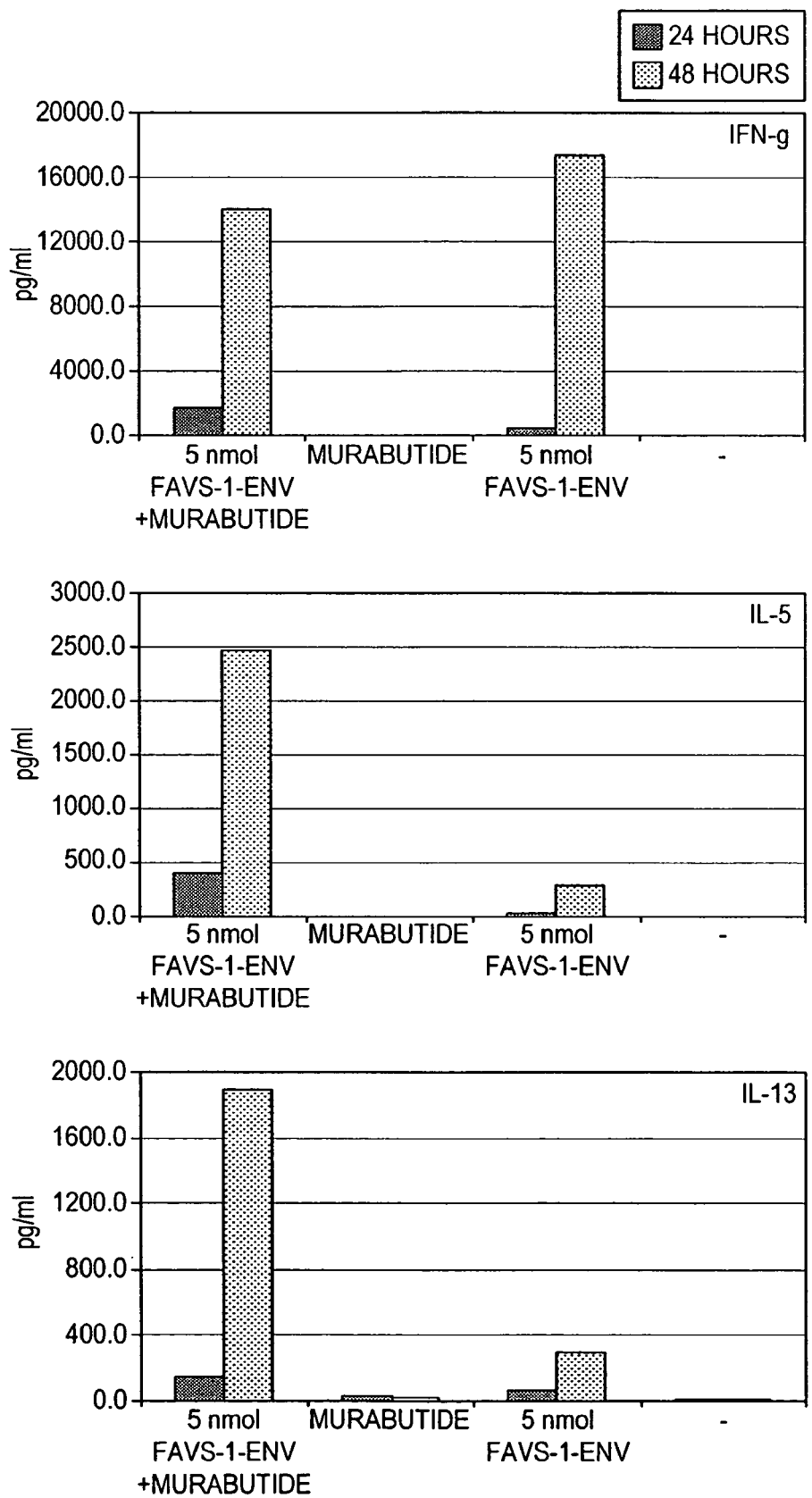

FAVS-1-ENV administered alone was shown to induce predominantly Th-1 cytokine production (i.e. IL-2 and IFN-g) with low levels of Th-2 cytokines also being produced. The inclusion of murabutide within the formulation led to the induction of a more balanced Th-1/Th-2 response with higher levels of Th-2 cytokines such as IL-5, IL-10 and IL-13 (FIG. 8).

Example 5

Immunogenicity of Fluorocarbon-Vectored Peptides Administered Mucosally

Specific-pathogen-free mice (6-8 week female Balb/c) were purchased from Harlan (UK).

FAVS-1-ENV (50 nmoles per mouse) was administered twice intranasally in 0.01M PBS alone or in combination with 100 µg of Murabutide with 10 days interval between both administration. Mice were slightly anaesthetised with Isoflurane (Isoflo, Solvay, UK). 20 µl of soluble peptide solution (10 µl/nostril) was administered using a micropipette. A control group received PBS only. Each dosing group comprised six animals. Mice were sacrificed 10 days after the last administration by carbon dioxide asphyxiation. Spleens were removed, pooled for each group of mice and spleen cells were isolated. Cells were washed three times with RPMI-1640 before counting. Counting was performed using a Thomas counting slide. Spleen cells from individual mice were cultured with the appropriate concentration of peptide (10 or 0 µg/ml of T helper ENV (301-322) or P18-I10 CTL epitope) in culture medium during 18 hours at 37° C. under 5% $CO_2$ atmosphere. IFN-g Elispot assay was then performed using the Diaclone Kit as described in Example 3. The spots were counted using a Carl Zeiss Vision Elispot reader unit. The results correspond to mean values obtained with each conditions after background subtraction (<10 spots). Results are expressed as spot forming units (SFC) per million input spleen cells. The data represent the average for 6 mice.

Figure 9:
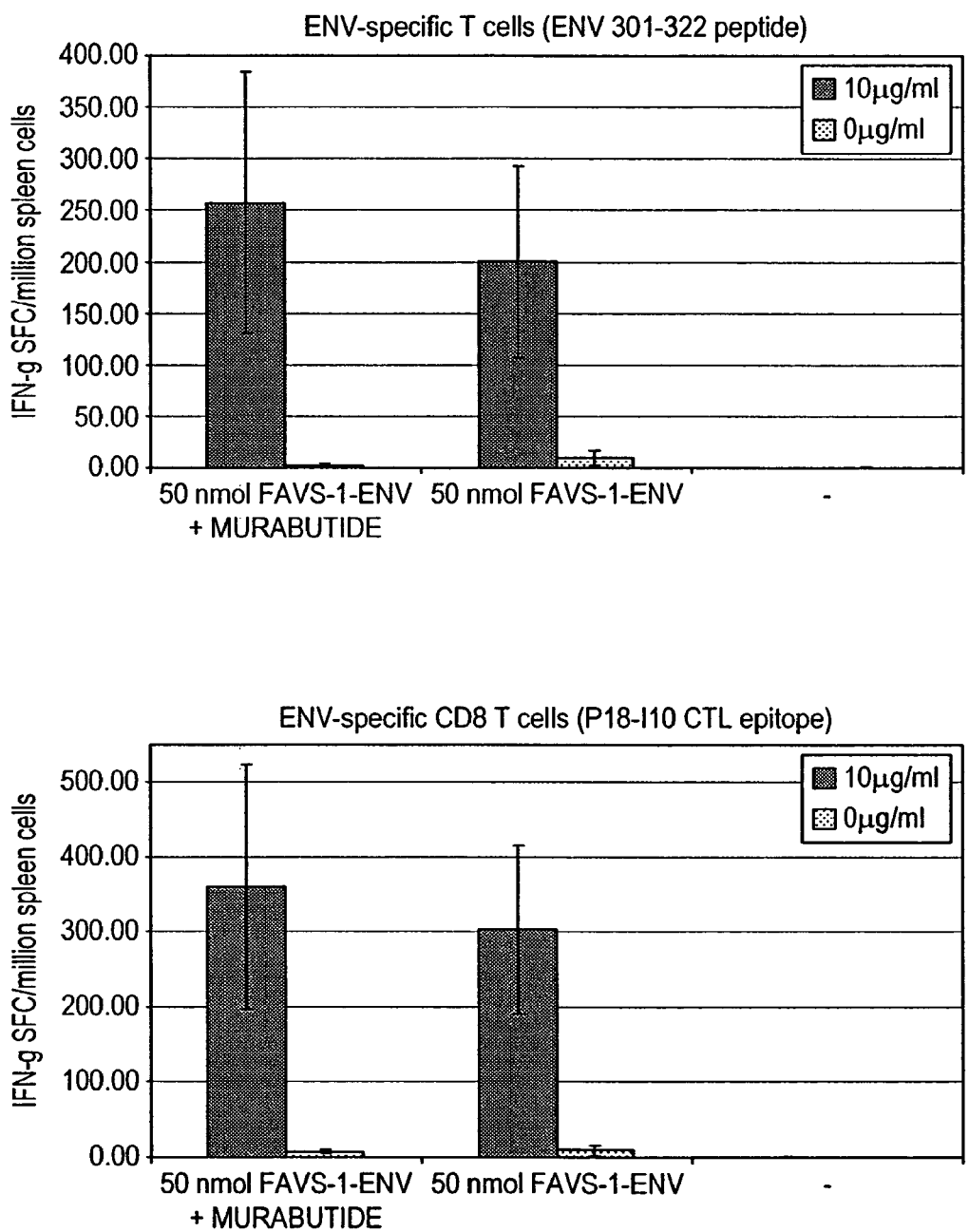
FIG. 9: shows cellular immune response assessed by ex vivo IFN-g ELISPOT assay in mice after two intranasal administrations with FAVS-1-ENV alone or in combination with murabutide.

All six mice per group immunised intranasally either with FAVS-1-ENV alone or in combination with murabutide produced a robust systemic T-cell response. Combination with murabutide led to modest increases in the frequency of IFN-gamma producing T cells (FIG. 9).

Example 6

Example HIV Peptides

Candidate peptides for attachment to the fluorocarbon vector to produce a prophylactic or therapeutic vaccine for HIV may include the following one or more peptides or fragments thereof, or homologues (including the corresponding consensus, ancestral or central tree sequences from HIV-1 representing different clades such as but not limited to clades A, B, C, D, F, G and H as referred to in the 2004 Los Alamos National Laboratory database) or natural and non-natural variants thereof, but not necessarily exclusively. The standard one letter and three-letter amino acid codes have been utilised. Homologues have at least a 50% identity compared to a reference sequence. Preferably a homologue has 80, 85, 90, 95, 98 or 99% identity to a naturally occurring sequence. The sequences provided below are 35 amino acids in length. Fragments of these sequences that contain one or more epitopes are also candidate peptides for attachment to the fluorocarbon vector.

```
SEQ ID No 1
WKGEGAVVIQDNSDIKVVPRRKAKIIRDYGKQMAG
Trp-Lys-Gly-Glu-Gly-Ala-Val-Val-Ile-Gln-Asp-Asn-
Ser-Asp-Ile-Lys-Val-Val-Pro-Arg-Arg-Lys-Ala-Lys-
Ile-Ile-Arg-Asp-Tyr-Gly-Lys-Gln-Met-Ala-Gly

SEQ ID No 2
EIYKRWIILGLNKIVRMYSPTSILDIRQGPKEPFR
Glu-Ile-Tyr-Lys-Arg-Trp-Ile-Ile-Leu-Gly-Leu-Asn-
Lys-Ile-Val-Arg-Met-Tyr-Ser-Pro-Thr-Ser-Ile-Leu-
Asp-Ile-Arg-Gln-Gly-Pro-Lys-Glu-Pro-Phe-Arg

SEQ ID No 3
EHLKTAVQMAVFIHNFKRKGGIGGYSAGERIVDII
Glu-His-Leu-Lys-Thr-Ala-Val-Gln-Met-Ala-Val-Phe-
Ile-His-Asn-Phe-Lys-Arg-Lys-Gly-Gly-Ile-Gly-Gly-
Tyr-Ser-Ala-Gly-Glu-Arg-Ile-Val-Asp-Ile-Ile

SEQ ID No 4
WEFVNTPPLVKLWYQLEKEPIVGAETFYVDGAANR
Trp-Glu-Phe-Val-Asn-Thr-Pro-Pro-Leu-Val-Lys-Leu-
Trp-Tyr-Gln-Leu-Glu-Lys-Glu-Pro-Ile-Val-Gly-Ala-
Glu-Thr-Phe-Tyr-Val-Asp-Gly-Ala-Ala-Asn-Arg

SEQ ID No 5
GERIVDIIATDIQTKELQKQITKIQNFRVYYRDSR
Gly-Glu-Arg-Ile-Val-Asp-Ile-Ile-Ala-Thr-Asp-Ile-
Gln-Thr-Lys-Glu-Leu-Gln-Lys-Gln-Ile-Thr-Lys-Ile-
Gln-Asn-Phe-Arg-Val-Tyr-Tyr-Arg-Asp-Ser-Arg

SEQ ID No 6
FRKYTAFTIPSINNETPGIRYQYNVLPQGWKGSPA
Phe-Arg-Lys-Tyr-Thr-Ala-Phe-Thr-Ile-Pro-Ser-Ile-
Asn-Asn-Glu-Thr-Pro-Gly-Ile-Arg-Tyr-Gln-Tyr-Asn-
Val-Leu-Pro-Gln-Gly-Trp-Lys-Gly-Ser-Pro-Ala

SEQ ID No 7
NWFDITNWLWYIKIFIMIVGGLIGLRIVFAVLSIV
Asn-Trp-Phe-Asp-Ile-Thr-Asn-Trp-Leu-Trp-Tyr-Ile-
Lys-Ile-Phe-Ile-Met-Ile-Val-Gly-Gly-Leu-Ile-Gly-
Leu-Arg-Ile-Val-Phe-Ala-Val-Leu-Ser-Ile-Val

SEQ ID No 8
ENPYNTPVFAIKKKDSTKWRKLVDFRELNKRTQDF
Glu-Asn-Pro-Tyr-Asn-Thr-Pro-Val-Phe-Ala-Ile-Lys-
Lys-Lys-Asp-Ser-Thr-Lys-Trp-Arg-Lys-Leu-Val-Asp-
Phe-Arg-Glu-Leu-Asn-Lys-Arg-Thr-Gln-Asp-Phe

SEQ ID No 9
VASGYIEAEVIPAETGQETAYFLLKLAGRWPVKTI
Val-Ala-Ser-Gly-Tyr-Ile-Glu-Ala-Glu-Val-Ile-Pro-
Ala-Glu-Thr-Gly-Gln-Glu-Thr-Ala-Tyr-Phe-Leu-Leu-
Lys-Leu-Ala-Gly-Arg-Trp-Pro-Val-Lys-Thr-Ile

SEQ ID No 10
PDKSESELVSQIIEQLIKKEKVYLAWVPAHKGIGG
Pro-Asp-Lys-Ser-Glu-Ser-Glu-Leu-Val-Ser-Gln-Ile-
Ile-Glu-Gln-Leu-Ile-Lys-Lys-Glu-Lys-Val-Tyr-Leu-
Ala-Trp-Val-Pro-Ala-His-Lys-Gly-Ile-Gly-Gly
```

SEQ ID No 11
NRWQVMIVWQVDRMRIRTWKSLVKHHMYISRKAKG
Asn-Arg-Trp-Gln-Val-Met-Ile-Val-Trp-Gln-Val-Asp-
Arg-Met-Arg-Ile-Arg-Thr-Trp-Lys-Ser-Leu-Val-Lys-
His-His-Met-Tyr-Ile-Ser-Arg-Lys-Ala-Lys-Gly SEQ ID No 12
HPDKWTVQPIVLPEKDSWTVNDIQKLVGKLNWASQ
His-Pro-Asp-Lys-Trp-Thr-Val-Gln-Pro-Ile-Val-Leu-
Pro-Glu-Lys-Asp-Ser-Trp-Thr-Val-Asn-Asp-Ile-Gln-
Lys-Leu-Val-Gly-Lys-Leu-Asn-Trp-Ala-Ser-Gln SEQ ID No 13
PAIFQSSMTKILEPFRKQNPDIVIYQYMDDLYVGS
Pro-Ala-Ile-Phe-Gln-Ser-Ser-Met-Thr-Lys-Ile-Leu-
Glu-Pro-Phe-Arg-Lys-Gln-Asn-Pro-Asp-Ile-Val-Ile-
Tyr-Gln-Tyr-Met-Asp-Asp-Leu-Tyr-Val-Gly-Ser SEQ ID No 14
MRGAHTNDVKQLTEAVQKIATESIVIWGKTPKFKL
Met-Arg-Gly-Ala-His-Thr-Asn-Asp-Val-Lys-Gln-Leu-
Thr-Glu-Ala-Val-Gln-Lys-Ile-Ala-Thr-Glu-Ser-Ile-
Val-Ile-Trp-Gly-Lys-Thr-Pro-Lys-Phe-Lys-Leu SEQ ID No 15
EKAFSPEVIPMFSALSEGATPQDLNTMLNTVGGHQ
Glu-Lys-Ala-Phe-Ser-Pro-Glu-Val-Ile-Pro-Met-Phe-
Ser-Ala-Leu-Ser-Glu-Gly-Ala-Thr-Pro-Gln-Asp-Leu-
Asn-Thr-Met-Leu-Asn-Thr-Val-Gly-Gly-His-Gln SEQ ID No 16
NLLRAIEAQQHLLQLTVWGIKQLQARVLAVERYLK
Asn-Leu-Leu-Arg-Ala-Ile-Glu-Ala-Gln-Gln-His-Leu-
Leu-Gln-Leu-Thr-Val-Trp-Gly-Ile-Lys-Gln-Leu-Gln-
Ala-Arg-Val-Leu-Ala-Val-Glu-Arg-Tyr-Leu-Lys SEQ ID No 17
ASVLSGGELDRWEKIRLRPGGKKKYKLKHIVWASR
Ala-Ser-Val-Leu-Ser-Gly-Gly-Glu-Leu-Asp-Arg-Trp-
Glu-Lys-Ile-Arg-Leu-Arg-Pro-Gly-Gly-Lys-Lys-Lys-
Tyr-Lys-Leu-Lys-His-Ile-Val-Trp-Ala-Ser-Arg SEQ ID No 18
ELYKYKVVKIEPLGVAPTKAKRRVVQREKRAVGIG
Glu-Leu-Tyr-Lys-Tyr-Lys-Val-Val-Lys-Ile-Glu-Pro-
Leu-Gly-Val-Ala-Pro-Thr-Lys-Ala-Lys-Arg-Arg-Val-
Val-Gln-Arg-Glu-Lys-Arg-Ala-Val-Gly-Ile-Gly SEQ ID No 19
FPISPIETVPVKLKPGMDGPKVKQWPLTEEKIKAL
Phe-Pro-Ile-Ser-Pro-Ile-Glu-Thr-Val-Pro-Val-Lys-
Leu-Lys-Pro-Gly-Met-Asp-Gly-Pro-Lys-Val-Lys-Gln-
Trp-Pro-Leu-Thr-Glu-Glu-Lys-Ile-Lys-Ala-Leu SEQ ID No 20
QIYQEPFKNLKTGKYARMRGAHTNDVKQLTEAVQK
Gln-Ile-Tyr-Gln-Glu-Pro-Phe-Lys-Asn-Leu-Lys-Thr-
Gly-Lys-Tyr-Ala-Arg-Met-Arg-Gly-Ala-His-Thr-Asn-
Asp-Val-Lys-Gln-Leu-Thr-Glu-Ala-Val-Gln-Lys SEQ ID No 21
NLLRAIEAQQHLLQLTVWGIKQLQARVLAVERYLK
Asn-Leu-Leu-Arg-Ala-Ile-Glu-Ala-Gln-Gln-His-Leu-
Leu-Gln-Leu-Thr-Val-Trp-Gly-Ile-Lys-Gln-Leu-Gln-
Ala-Arg-Val-Leu-Ala-Val-Glu-Arg-Tyr-Leu-Lys SEQ ID No 22
AGLKKKKSVTVLDVGDAYFSVPLDKDFRKYTAFTI
Ala-Gly-Leu-Lys-Lys-Lys-Lys-Ser-Val-Thr-Val-Leu-
Asp-Val-Gly-Asp-Ala-Tyr-Phe-Ser-Val-Pro-Leu-Asp-
Lys-Asp-Phe-Arg-Lys-Tyr-Thr-Ala-Phe-Thr-Ile SEQ ID No 23
TTNQKTELQATHLALQDSGLEVNIVTDSQYALGII
Thr-Thr-Asn-Gln-Lys-Thr-Glu-Leu-Gln-Ala-Ile-His-
Leu-Ala-Leu-Gln-Asp-Ser-Gly-Leu-Glu-Val-Asn-Ile-
Val-Thr-Asp-Ser-Gln-Tyr-Ala-Leu-Gly-Ile-Ile SEQ ID No 24
VSQNYPIVQNLQGQMVHQAISPRTLNAWVKVVEEK
Val-Ser-Gln-Asn-Tyr-Pro-Ile-Val-Gln-Asn-Leu-Gln-
Gly-Gln-Met-Val-His-Gln-Ala-Ile-Ser-Pro-Arg-Thr-
Leu-Asn-Ala-Trp-Val-Lys-Val-Val-Glu-Glu-Lys SEQ ID No 25
EAELELAENREILKEPVHGVYYDPSKDLIAEIQKQ
Glu-Ala-Glu-Leu-Glu-Leu-Ala-Glu-Asn-Arg-Glu-Ile-
Leu-Lys-Glu-Pro-Val-His-Gly-Val-Tyr-Tyr-Asp-Pro-
Ser-Lys-Asp-Leu-Ile-Ala-Glu-Ile-Gln-Lys-Gln SEQ ID No 26
TPDKKHQKEPPFLWMGYELHPDKWTVQPIVLPEKD
Thr-Pro-Asp-Lys-Lys-His-Gln-Lys-Glu-Pro-Pro-Phe-
Leu-Trp-Met-Gly-Tyr-Glu-Leu-His-Pro-Asp-Lys-Trp-
Thr-Val-Gln-Pro-Ile-Val-Leu-Pro-Glu-Lys-Asp SEQ ID No 27
EPFRDYVDRFYKTLRAEQASQEVKNWMTETLLVQN
Glu-Pro-Phe-Arg-Asp-Tyr-Val-Asp-Arg-Phe-Tyr-Lys-
Thr-Leu-Arg-Ala-Glu-Gln-Ala-Ser-Gln-Glu-Val-Lys-
Asn-Trp-Met-Thr-Glu-Thr-Leu-Leu-Val-Gln-Asn SEQ ID No 28
NEWTLELLEELKSEAVRHFPRIWLHGLGQHIYETY
Asn-Glu-Trp-Thr-Leu-Glu-Leu-Leu-Glu-Glu-Leu-Lys-
Ser-Glu-Ala-Val-Arg-His-Phe-Pro-Arg-Ile-Trp-Leu-
His-Gly-Leu-Gly-Gln-His-Ile-Tyr-Glu-Thr-Tyr SEQ ID No 29
EGLIYSQKRQDILDLWVYHTQGYFPDWQNYTPGPG
Glu-Gly-Leu-Ile-Tyr-Ser-Gln-Lys-Arg-Gln-Asp-Ile-
Leu-Asp-Leu-Trp-Val-Tyr-His-Thr-Gln-Gly-Tyr-Phe-
Pro-Asp-Trp-Gln-Asn-Tyr-Thr-Pro-Gly-Pro-Gly SEQ ID No 30
HFLKEKGGLEGLIYSQKRQDILDLWVYHTQGYFPD
His-Phe-Leu-Lys-Glu-Lys-Gly-Gly-Leu-Glu-Gly-Leu-
Ile-Tyr-Ser-Gln-Lys-Arg-Gln-Asp-Ile-Leu-Asp-Leu-
Trp-Val-Tyr-His-Thr-Gln-Gly-Tyr-Phe-Pro-Asp SEQ ID No 31
FPVRPQVPLRPMTYKAAVDLSHFLKEKGGLEGLIY
Phe-Pro-Val-Arg-Pro-Gln-Val-Pro-Leu-Arg-Pro-Met-
Thr-Tyr-Lys-Ala-Ala-Val-Asp-Leu-Ser-His-Phe-Leu-
Lys-Glu-Lys-Gly-Gly-Leu-Glu-Gly-Leu-Ile-Tyr SEQ ID No 32
FPQITLWQRPLVTIKIGGQLKEALLDTGADDTVLE
Phe-Pro-Gln-Ile-Thr-Leu-Trp-Gln-Arg-Pro-Leu-Val-
Thr-Ile-Lys-Ile-Gly-Gly-Gln-Leu-Lys-Glu-Ala-Leu-
Leu-Asp-Thr-Gly-Ala-Asp-Asp-Thr-Val-Leu-Glu SEQ ID No 33
LVITTYWGLHTGERDWHLGQGVSIEWRKKRYSTQV
Leu-Val-Ile-Thr-Thr-Tyr-Trp-Gly-Leu-His-Thr-Gly-
Glu-Arg-Asp-Trp-His-Leu-Gly-Gln-Gly-Val-Ser-Ile-
Glu-Trp-Arg-Lys-Lys-Arg-Tyr-Ser-Thr-Gln-Val SEQ ID No 34
APPEESFRFGEETTTPSQKQEPIDKELYPLASLRS
Ala-Pro-Pro-Glu-Glu-Ser-Phe-Arg-Phe-Gly-Glu-Glu-
Thr-Thr-Thr-Pro-Ser-Gln-Lys-Gln-Glu-Pro-Ile-Asp-
Lys-Glu-Leu-Tyr-Pro-Leu-Ala-Ser-Leu-Arg-Ser SEQ ID No 35
KRRVVQREKRAVGIGAMFLGFLGAAGSTMGAASMT
Lys-Arg-Arg-Val-Val-Gln-Arg-Glu-Lys-Arg-Ala-Val-
Gly-Ile-Gly-Ala-Met-Phe-Leu-Gly-Phe-Leu-Gly-Ala-
Ala-Gly-Ser-Thr-Met-Gly-Ala-Ala-Ser-Met-Thr SEQ ID No 36
GLGQHIYETYGDTWAGVEAIIRILQQLLFIHFRIG
Gly-Leu-Gly-Gln-His-Ile-Tyr-Glu-Thr-Tyr-Gly-Asp-
Thr-Trp-Ala-Gly-Val-Glu-Ala-Ile-Ile-Arg-Ile-Leu-
Gln-Gln-Leu-Leu-Phe-Ile-His-Phe-Arg-Ile-Gly Candidate peptides for inclusion into a prophylactic or therapeutic vaccine for HIV may be peptides from any of the structural or functional domains Gag, Pol, Nef, Env, Vif, Vpr, Vpu, Tat or Rev in any such combination.

INCORPORATION BY REFERENCE

The entire disclosure of each of the publications, web sites and patent documents referred to herein is incorporated by reference in its entirety for all purposes to the same extent as if each individual publication, web site or patent document were so individually denoted.

EQUIVALENTS

The invention may be embodied in other specific forms without departing form the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A multi-component pharmaceutical composition configured for intracellular delivery of T cell epitopes to induce a cell-mediated immune response, the pharmaceutical composition comprising:

two to about 20 different types of fluorocarbon peptide constructs, wherein each different type of fluorocarbon peptide construct comprises:

a fluorocarbon chain from 3 to 30 carbon atoms, wherein one or more fluorine moieties is optionally substituted with chlorine, bromine or iodine or a methyl group; and, a peptide comprising one or more CD8+T cell epitopes including at least two MHC class I or II epitopes, the peptide being coupled to the fluorocarbon vector via either an N-terminus or C-terminus of the peptide and the fluorocarbon vector;

wherein the fluorocarbon peptide constructs are comprised within micelles, each different type of fluorocarbon peptide construct comprises a different peptide sequence, and the fluorocarbon chain enhances CD8+T cell response against the peptide; and, one or more pharmaceutical acceptable carriers, excipients, diluents or adjuvants.

2. The composition of claim 1 wherein the fluorocarbon peptide construct is according to structure where Sp is an optional chemical spacer moiety and R is the peptide.

3. The composition of claim 1 wherein the fluorocarbon peptide construct is according to structure

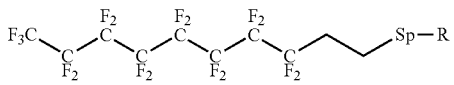

where Sp is an optional chemical spacer moiety and R is the peptide.

4. The composition of claim 1 wherein the fluorocarbon peptide construct is according to structure

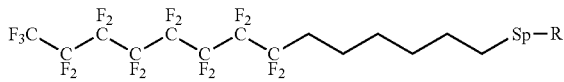

where Sp is an optional chemical spacer moiety and R is the peptide.

5. The composition of claim 1 wherein the peptide comprises one or more immunogenic epitopes from a viral protein.

6. The composition of claim 1 wherein the peptide comprises one or more immunogenic epitopes from an influenza or hepatitis B virus protein.

7. The composition of claim 1 wherein the peptide comprises between 7 to 70 amino acids.

8. The composition of claim 1 wherein the peptide comprises two or more overlapping T cell epitopes.

9. The composition of claim 1 wherein the peptide is an HIV epitope.

10. The composition of claim 1 wherein the peptide comprises multiple overlapping viral T cell epitopes and/or fusion peptides.

11. The composition of claim 1, wherein the fluorocarbon peptide construct is according to structure $C_mF_n$-$C_yH_x$-Sp)-R, where m=3 to 30, n<=2m+1, y=0 to 15, x<=2y, (m+y)=3-30 and Sp is an optional chemical spacer moiety and R is the peptide.

12. A combination of different types of fluorocarbon peptide constructs configured for intracellular delivery of T cell epitopes to induce a cell-mediated immune response, each different type of fluorocarbon peptide construct comprising:

a fluorocarbon chain from 3 to 20 carbon atoms, wherein one or more fluorine moieties is optionally substituted with chlorine, bromine or iodine or a methyl group, and an in vivo immunogenic peptide of between 7 to 70 amino acids in length, comprising one or more CD8+T cell epitopes, at least two MHC class I or MHC class II epitopes, and being covalently linked via either an N-terminus or C-terminus terminal lysine to the fluorocarbon chain, wherein each different type of fluorocarbon peptide construct comprises a different in vivo immunogenic peptide sequence and the fluorocarbon chain enhances CD8+T cell response against the peptide; and, wherein the combination of different types of the fluorocarbon constructs is lyophilized.

13. The fluorocarbon peptide construct of claim 12, wherein the peptide is between 15 to 35 amino acids in length.

14. The fluorocarbon peptide construct of claim 12, wherein the fluorocarbon peptide construct is according to structure $C_mF_n$—$C_yH_x$-Sp-R, where m=3 to 30, n<=2m+1, y=0 to 15, x<=2y, (m+y)=3-30 and Sp is an optional chemical spacer moiety and R is the peptide.

15. The fluorocarbon peptide construct of claim 12, wherein the fluorocarbon peptide construct is according to structure where Sp is an optional chemical spacer moiety and R is the peptide.

16. The fluorocarbon peptide construct of claim 12, wherein the peptide comprises one or more epitopes from an influenza or hepatitis B virus protein.

17. A multi-component pharmaceutical composition configured for intracellular delivery of T cell epitopes to induce a cell-mediated immune response, the pharmaceutical composition comprising:

two to about 20 different types of fluorocarbon peptide constructs, wherein each different type of fluorocarbon peptide construct comprises:

a fluorocarbon chain from 3 to 30 carbon atoms, wherein one or more fluorine moieties is substituted with chlorine, bromine or iodine or a methyl group; and, a peptide comprising one or more CD8+T cell epitopes including at least two MHC class I or II epitopes, the peptide being coupled to the fluorocarbon vector via either an N-terminus or C-terminus of the peptide and the fluorocarbon vector;

wherein the fluorocarbon peptide constructs are comprised within micelles, and wherein each different type of fluorocarbon peptide construct comprises a different peptide sequence, and the fluorocarbon chain enhances CD8+T cell response against the peptide; and, one or more pharmaceutical acceptable carriers, excipients, diluents or adjuvants.

18. The composition of claim 17, wherein the peptide comprises multiple overlapping viral T cell epitopes and/or fusion peptides.

19. The composition of claim 17 wherein the peptide comprises between 7 to 70 amino acids.

* * * * *

```
                         SEQUENCE LISTING

<160> NUMBER OF SEQ ID NOS: 40

<210> SEQ ID NO 1
<211> LENGTH: 35
<212> TYPE: PRT
<213> ORGANISM: Human immunodeficiency virus type 1

<400> SEQUENCE: 1

Trp Lys Gly Glu Gly Ala Val Val Ile Gln Asp Asn Ser Asp Ile Lys
1               5                   10                  15

Val Val Pro Arg Arg Lys Ala Lys Ile Ile Arg Asp Tyr Gly Lys Gln
            20                  25                  30

Met Ala Gly
        35

<210> SEQ ID NO 2
<211> LENGTH: 35
<212> TYPE: PRT
<213> ORGANISM: Human immunodeficiency virus type 1

<400> SEQUENCE: 2

Glu Ile Tyr Lys Arg Trp Ile Ile Leu Gly Leu Asn Lys Ile Val Arg
1               5                   10                  15

Met Tyr Ser Pro Thr Ser Ile Leu Asp Ile Arg Gln Gly Pro Lys Glu
            20                  25                  30

Pro Phe Arg
        35

<210> SEQ ID NO 3
<211> LENGTH: 35
<212> TYPE: PRT
<213> ORGANISM: Human immunodeficiency virus type 1

<400> SEQUENCE: 3

Glu His Leu Lys Thr Ala Val Gln Met Ala Val Phe Ile His Asn Phe
1               5                   10                  15

Lys Arg Lys Gly Gly Ile Gly Gly Tyr Ser Ala Gly Glu Arg Ile Val
            20                  25                  30

Asp Ile Ile
        35

<210> SEQ ID NO 4
<211> LENGTH: 35
<212> TYPE: PRT
<213> ORGANISM: Human immunodeficiency virus type 1

<400> SEQUENCE: 4

Trp Glu Phe Val Asn Thr Pro Pro Leu Val Lys Leu Trp Tyr Gln Leu
1               5                   10                  15
```

```
Glu Lys Glu Pro Ile Val Gly Ala Glu Thr Phe Tyr Val Asp Gly Ala
                20                  25                  30

Ala Asn Arg
        35

<210> SEQ ID NO 5
<211> LENGTH: 35
<212> TYPE: PRT
<213> ORGANISM: Human immunodeficiency virus type 1

<400> SEQUENCE: 5

Gly Glu Arg Ile Val Asp Ile Ile Ala Thr Asp Ile Gln Thr Lys Glu
1               5                   10                  15

Leu Gln Lys Gln Ile Thr Lys Ile Gln Asn Phe Arg Val Tyr Tyr Arg
                20                  25                  30

Asp Ser Arg
        35

<210> SEQ ID NO 6
<211> LENGTH: 35
<212> TYPE: PRT
<213> ORGANISM: Human immunodeficiency virus type 1

<400> SEQUENCE: 6

Phe Arg Lys Tyr Thr Ala Phe Thr Ile Pro Ser Ile Asn Asn Glu Thr
1               5                   10                  15

Pro Gly Ile Arg Tyr Gln Tyr Asn Val Leu Pro Gln Gly Trp Lys Gly
                20                  25                  30

Ser Pro Ala
        35

<210> SEQ ID NO 7
<211> LENGTH: 35
<212> TYPE: PRT
<213> ORGANISM: Human immunodeficiency virus type 1

<400> SEQUENCE: 7

Asn Trp Phe Asp Ile Thr Asn Trp Leu Trp Tyr Ile Lys Ile Phe Ile
1               5                   10                  15

Met Ile Val Gly Gly Leu Ile Gly Leu Arg Ile Val Phe Ala Val Leu
                20                  25                  30

Ser Ile Val
        35

<210> SEQ ID NO 8
<211> LENGTH: 35
<212> TYPE: PRT
<213> ORGANISM: Human immunodeficiency virus type 1

<400> SEQUENCE: 8

Glu Asn Pro Tyr Asn Thr Pro Val Phe Ala Ile Lys Lys Lys Asp Ser
1               5                   10                  15

Thr Lys Trp Arg Lys Leu Val Asp Phe Arg Glu Leu Asn Lys Arg Thr
                20                  25                  30

Gln Asp Phe
        35

<210> SEQ ID NO 9
<211> LENGTH: 35
<212> TYPE: PRT
```

<213> ORGANISM: Human immunodeficiency virus type 1

<400> SEQUENCE: 9

Val Ala Ser Gly Tyr Ile Glu Ala Glu Val Ile Pro Ala Glu Thr Gly
1               5                   10                  15
Gln Glu Thr Ala Tyr Phe Leu Leu Lys Leu Ala Gly Arg Trp Pro Val
            20                  25                  30
Lys Thr Ile
        35

<210> SEQ ID NO 10
<211> LENGTH: 35
<212> TYPE: PRT
<213> ORGANISM: Human immunodeficiency virus type 1

<400> SEQUENCE: 10

Pro Asp Lys Ser Glu Ser Glu Leu Val Ser Gln Ile Ile Glu Gln Leu
1               5                   10                  15
Ile Lys Lys Glu Lys Val Tyr Leu Ala Trp Val Pro Ala His Lys Gly
            20                  25                  30
Ile Gly Gly
        35

<210> SEQ ID NO 11
<211> LENGTH: 35
<212> TYPE: PRT
<213> ORGANISM: Human immunodeficiency virus type 1

<400> SEQUENCE: 11

Asn Arg Trp Gln Val Met Ile Val Trp Gln Val Asp Arg Met Arg Ile
1               5                   10                  15
Arg Thr Trp Lys Ser Leu Val Lys His His Met Tyr Ile Ser Arg Lys
            20                  25                  30
Ala Lys Gly
        35

<210> SEQ ID NO 12
<211> LENGTH: 35
<212> TYPE: PRT
<213> ORGANISM: Human immunodeficiency virus type 1

<400> SEQUENCE: 12

His Pro Asp Lys Trp Thr Val Gln Pro Ile Val Leu Pro Glu Lys Asp
1               5                   10                  15
Ser Trp Thr Val Asn Asp Ile Gln Lys Leu Val Gly Lys Leu Asn Trp
            20                  25                  30
Ala Ser Gln
        35

<210> SEQ ID NO 13
<211> LENGTH: 35
<212> TYPE: PRT
<213> ORGANISM: Human immunodeficiency virus type 1

<400> SEQUENCE: 13

Pro Ala Ile Phe Gln Ser Ser Met Thr Lys Ile Leu Glu Pro Phe Arg
1               5                   10                  15
Lys Gln Asn Pro Asp Ile Val Ile Tyr Gln Tyr Met Asp Asp Leu Tyr
            20                  25                  30
Val Gly Ser

<210> SEQ ID NO 14
<211> LENGTH: 35
<212> TYPE: PRT
<213> ORGANISM: Human immunodeficiency virus type 1

<400> SEQUENCE: 14

Met Arg Gly Ala His Thr Asn Asp Val Lys Gln Leu Thr Glu Ala Val
1               5                   10                  15

Gln Lys Ile Ala Thr Glu Ser Ile Val Ile Trp Gly Lys Thr Pro Lys
            20                  25                  30

Phe Lys Leu
        35

<210> SEQ ID NO 15
<211> LENGTH: 35
<212> TYPE: PRT
<213> ORGANISM: Human immunodeficiency virus type 1

<400> SEQUENCE: 15

Glu Lys Ala Phe Ser Pro Glu Val Ile Pro Met Phe Ser Ala Leu Ser
1               5                   10                  15

Glu Gly Ala Thr Pro Gln Asp Leu Asn Thr Met Leu Asn Thr Val Gly
            20                  25                  30

Gly His Gln
        35

<210> SEQ ID NO 16
<211> LENGTH: 35
<212> TYPE: PRT
<213> ORGANISM: Human immunodeficiency virus type 1

<400> SEQUENCE: 16

Asn Leu Leu Arg Ala Ile Glu Ala Gln Gln His Leu Leu Gln Leu Thr
1               5                   10                  15

Val Trp Gly Ile Lys Gln Leu Gln Ala Arg Val Leu Ala Val Glu Arg
            20                  25                  30

Tyr Leu Lys
        35

<210> SEQ ID NO 17
<211> LENGTH: 35
<212> TYPE: PRT
<213> ORGANISM: Human immunodeficiency virus type 1

<400> SEQUENCE: 17

Ala Ser Val Leu Ser Gly Gly Glu Leu Asp Arg Trp Glu Lys Ile Arg
1               5                   10                  15

Leu Arg Pro Gly Gly Lys Lys Lys Tyr Lys Leu Lys His Ile Val Trp
            20                  25                  30

Ala Ser Arg
        35

<210> SEQ ID NO 18
<211> LENGTH: 35
<212> TYPE: PRT
<213> ORGANISM: Human immunodeficiency virus type 1

<400> SEQUENCE: 18

Glu Leu Tyr Lys Tyr Lys Val Val Lys Ile Glu Pro Leu Gly Val Ala

```
1               5                   10                  15
Pro Thr Lys Ala Lys Arg Arg Val Val Gln Arg Glu Lys Arg Ala Val
            20                  25                  30

Gly Ile Gly
        35

<210> SEQ ID NO 19
<211> LENGTH: 35
<212> TYPE: PRT
<213> ORGANISM: Human immunodeficiency virus type 1

<400> SEQUENCE: 19

Phe Pro Ile Ser Pro Ile Glu Thr Val Pro Val Lys Leu Lys Pro Gly
1               5                   10                  15

Met Asp Gly Pro Lys Val Lys Gln Trp Pro Leu Thr Glu Glu Lys Ile
            20                  25                  30

Lys Ala Leu
        35

<210> SEQ ID NO 20
<211> LENGTH: 35
<212> TYPE: PRT
<213> ORGANISM: Human immunodeficiency virus type 1

<400> SEQUENCE: 20

Gln Ile Tyr Gln Glu Pro Phe Lys Asn Leu Lys Thr Gly Lys Tyr Ala
1               5                   10                  15

Arg Met Arg Gly Ala His Thr Asn Asp Val Lys Gln Leu Thr Glu Ala
            20                  25                  30

Val Gln Lys
        35

<210> SEQ ID NO 21
<211> LENGTH: 35
<212> TYPE: PRT
<213> ORGANISM: Human immunodeficiency virus type 1

<400> SEQUENCE: 21

Asn Leu Leu Arg Ala Ile Glu Ala Gln Gln His Leu Leu Gln Leu Thr
1               5                   10                  15

Val Trp Gly Ile Lys Gln Leu Gln Ala Arg Val Leu Ala Val Glu Arg
            20                  25                  30

Tyr Leu Lys
        35

<210> SEQ ID NO 22
<211> LENGTH: 35
<212> TYPE: PRT
<213> ORGANISM: Human immunodeficiency virus type 1

<400> SEQUENCE: 22

Ala Gly Leu Lys Lys Lys Lys Ser Val Thr Val Leu Asp Val Gly Asp
1               5                   10                  15

Ala Tyr Phe Ser Val Pro Leu Asp Lys Asp Phe Arg Lys Tyr Thr Ala
            20                  25                  30

Phe Thr Ile
        35

<210> SEQ ID NO 23
<211> LENGTH: 35
```

-continued

```
<212> TYPE: PRT
<213> ORGANISM: Human immunodeficiency virus type 1

<400> SEQUENCE: 23

Thr Thr Asn Gln Lys Thr Glu Leu Gln Ala Ile His Leu Ala Leu Gln
1               5                   10                  15

Asp Ser Gly Leu Glu Val Asn Ile Val Thr Asp Ser Gln Tyr Ala Leu
            20                  25                  30

Gly Ile Ile
        35

<210> SEQ ID NO 24
<211> LENGTH: 35
<212> TYPE: PRT
<213> ORGANISM: Human immunodeficiency virus type 1

<400> SEQUENCE: 24

Val Ser Gln Asn Tyr Pro Ile Val Gln Asn Leu Gln Gly Gln Met Val
1               5                   10                  15

His Gln Ala Ile Ser Pro Arg Thr Leu Asn Ala Trp Val Lys Val Val
            20                  25                  30

Glu Glu Lys
        35

<210> SEQ ID NO 25
<211> LENGTH: 35
<212> TYPE: PRT
<213> ORGANISM: Human immunodeficiency virus type 1

<400> SEQUENCE: 25

Glu Ala Glu Leu Glu Leu Ala Glu Asn Arg Glu Ile Leu Lys Glu Pro
1               5                   10                  15

Val His Gly Val Tyr Tyr Asp Pro Ser Lys Asp Leu Ile Ala Glu Ile
            20                  25                  30

Gln Lys Gln
        35

<210> SEQ ID NO 26
<211> LENGTH: 35
<212> TYPE: PRT
<213> ORGANISM: Human immunodeficiency virus type 1

<400> SEQUENCE: 26

Thr Pro Asp Lys Lys His Gln Lys Glu Pro Pro Phe Leu Trp Met Gly
1               5                   10                  15

Tyr Glu Leu His Pro Asp Lys Trp Thr Val Gln Pro Ile Val Leu Pro
            20                  25                  30

Glu Lys Asp
        35

<210> SEQ ID NO 27
<211> LENGTH: 35
<212> TYPE: PRT
<213> ORGANISM: Human immunodeficiency virus type 1

<400> SEQUENCE: 27

Glu Pro Phe Arg Asp Tyr Val Asp Arg Phe Tyr Lys Thr Leu Arg Ala
1               5                   10                  15

Glu Gln Ala Ser Gln Glu Val Lys Asn Trp Met Thr Glu Thr Leu Leu
            20                  25                  30
```

Val Gln Asn
        35

<210> SEQ ID NO 28
<211> LENGTH: 35
<212> TYPE: PRT
<213> ORGANISM: Human immunodeficiency virus type 1

<400> SEQUENCE: 28

Asn Glu Trp Thr Leu Glu Leu Leu Glu Leu Lys Ser Glu Ala Val
1               5                   10                  15

Arg His Phe Pro Arg Ile Trp Leu His Gly Leu Gly Gln His Ile Tyr
            20                  25                  30

Glu Thr Tyr
        35

<210> SEQ ID NO 29
<211> LENGTH: 35
<212> TYPE: PRT
<213> ORGANISM: Human immunodeficiency virus type 1

<400> SEQUENCE: 29

Glu Gly Leu Ile Tyr Ser Gln Lys Arg Gln Asp Ile Leu Asp Leu Trp
1               5                   10                  15

Val Tyr His Thr Gln Gly Tyr Phe Pro Asp Trp Gln Asn Tyr Thr Pro
            20                  25                  30

Gly Pro Gly
        35

<210> SEQ ID NO 30
<211> LENGTH: 35
<212> TYPE: PRT
<213> ORGANISM: Human immunodeficiency virus type 1

<400> SEQUENCE: 30

His Phe Leu Lys Glu Lys Gly Gly Leu Glu Gly Leu Ile Tyr Ser Gln
1               5                   10                  15

Lys Arg Gln Asp Ile Leu Asp Leu Trp Val Tyr His Thr Gln Gly Tyr
            20                  25                  30

Phe Pro Asp
        35

<210> SEQ ID NO 31
<211> LENGTH: 35
<212> TYPE: PRT
<213> ORGANISM: Human immunodeficiency virus type 1

<400> SEQUENCE: 31

Phe Pro Val Arg Pro Gln Val Pro Leu Arg Pro Met Thr Tyr Lys Ala
1               5                   10                  15

Ala Val Asp Leu Ser His Phe Leu Lys Glu Lys Gly Gly Leu Glu Gly
            20                  25                  30

Leu Ile Tyr
        35

<210> SEQ ID NO 32
<211> LENGTH: 35
<212> TYPE: PRT
<213> ORGANISM: Human immunodeficiency virus type 1

<400> SEQUENCE: 32

```
Phe Pro Gln Ile Thr Leu Trp Gln Arg Pro Leu Val Thr Ile Lys Ile
1               5                   10                  15

Gly Gly Gln Leu Lys Glu Ala Leu Leu Asp Thr Gly Ala Asp Asp Thr
            20                  25                  30

Val Leu Glu
        35

<210> SEQ ID NO 33
<211> LENGTH: 35
<212> TYPE: PRT
<213> ORGANISM: Human immunodeficiency virus type 1

<400> SEQUENCE: 33

Leu Val Ile Thr Thr Tyr Trp Gly Leu His Thr Gly Glu Arg Asp Trp
1               5                   10                  15

His Leu Gly Gln Gly Val Ser Ile Glu Trp Arg Lys Lys Arg Tyr Ser
            20                  25                  30

Thr Gln Val
        35

<210> SEQ ID NO 34
<211> LENGTH: 35
<212> TYPE: PRT
<213> ORGANISM: Human immunodeficiency virus type 1

<400> SEQUENCE: 34

Ala Pro Pro Glu Glu Ser Phe Arg Phe Gly Glu Glu Thr Thr Thr Pro
1               5                   10                  15

Ser Gln Lys Gln Glu Pro Ile Asp Lys Glu Leu Tyr Pro Leu Ala Ser
            20                  25                  30

Leu Arg Ser
        35

<210> SEQ ID NO 35
<211> LENGTH: 35
<212> TYPE: PRT
<213> ORGANISM: Human immunodeficiency virus type 1

<400> SEQUENCE: 35

Lys Arg Arg Val Val Gln Arg Glu Lys Arg Ala Val Gly Ile Gly Ala
1               5                   10                  15

Met Phe Leu Gly Phe Leu Gly Ala Ala Gly Ser Thr Met Gly Ala Ala
            20                  25                  30

Ser Met Thr
        35

<210> SEQ ID NO 36
<211> LENGTH: 35
<212> TYPE: PRT
<213> ORGANISM: Human immunodeficiency virus type 1

<400> SEQUENCE: 36

Gly Leu Gly Gln His Ile Tyr Glu Thr Tyr Gly Asp Thr Trp Ala Gly
1               5                   10                  15

Val Glu Ala Ile Ile Arg Ile Leu Gln Gln Leu Leu Phe Ile His Phe
            20                  25                  30

Arg Ile Gly
        35

<210> SEQ ID NO 37
```

-continued

```
<211> LENGTH: 22
<212> TYPE: PRT
<213> ORGANISM: Human immunodeficiency virus type 1

<400> SEQUENCE: 37

Asn Asn Thr Arg Lys Arg Ile Arg Ile Gln Arg Gly Pro Gly Arg Ala
1               5                   10                  15

Phe Val Thr Ile Gly Lys
            20

<210> SEQ ID NO 38
<211> LENGTH: 22
<212> TYPE: PRT
<213> ORGANISM: Human immunodeficiency virus type 1
<220> FEATURE:
<221> NAME/KEY: MISC_FEATURE
<223> OTHER INFORMATION: Peptide sequence of a fluorocarbon-vector
      peptide

<400> SEQUENCE: 38

Asn Asn Thr Arg Lys Arg Ile Arg Ile Gln Arg Gly Pro Gly Arg Ala
1               5                   10                  15

Phe Val Thr Ile Gly Lys
            20

<210> SEQ ID NO 39
<211> LENGTH: 17
<212> TYPE: PRT
<213> ORGANISM: Human immunodeficiency virus type 1
<220> FEATURE:
<221> NAME/KEY: MISC_FEATURE
<223> OTHER INFORMATION: Peptide sequence of a fluorocarbon vector
      peptide

<400> SEQUENCE: 39

Ile Arg Ile Gln Arg Gly Pro Gly Arg Ala Phe Val Thr Ile Gly Lys
1               5                   10                  15

Lys

<210> SEQ ID NO 40
<211> LENGTH: 10
<212> TYPE: PRT
<213> ORGANISM: Human immunodeficiency virus type 1

<400> SEQUENCE: 40

Arg Gly Pro Gly Arg Ala Phe Val Thr Ile
1               5                   10
```